United States Patent [19]

Hogan

[11] Patent Number: 5,054,290
[45] Date of Patent: Oct. 8, 1991

[54] PORTABLE, SUPERABSORBENT CARRYING CONTAINER ABLE TO PROVIDE REFRIGERATION FOR ITS CONTENTS ON-DEMAND

[75] Inventor: John D. Hogan, Gloucester, Mass.

[73] Assignee: Beth Israel Hospital Assoc., Boston, Mass.

[21] Appl. No.: 539,929

[22] Filed: Jun. 18, 1990

Related U.S. Application Data

[63] Continuation-in-part of Ser. No. 529,566, May 25, 1990, which is a continuation-in-part of Ser. No. 445,008, Dec. 4, 1989, which is a continuation-in-part of Ser. No. 142,077, Jan. 11, 1988, Pat. No. 4,885,000, which is a continuation-in-part of Ser. No. 001,648, Jan. 9, 1987, abandoned.

[51] Int. Cl.$^5$ ............................................. F17C 1/00
[52] U.S. Cl. ..................................... 62/45.1; 62/457.2
[58] Field of Search ..................... 62/45.1, 457.1, 457.2

[56] References Cited

U.S. PATENT DOCUMENTS

| | | | |
|---|---|---|---|
| 2,994,452 | 8/1961 | Morrison | 62/45.1 |
| 3,717,005 | 2/1973 | McGlew et al. | 62/45.1 |
| 4,287,720 | 9/1981 | Barthel | 62/45.1 |
| 4,597,266 | 7/1986 | Entrekin | 62/46.1 |
| 4,802,344 | 2/1989 | Livingston et al. | 62/457.2 |

Primary Examiner—Ronald C. Capossela
Attorney, Agent, or Firm—David Prashker

[57] ABSTRACT

A portable and disposable, superabsorbent carrying container is provided which allows the user to obtain refrigeration on-demand for its contents. The container has a superabsorbent fibrous lining which absorbs not less than 15 times its own weight of fluids. In addition, the carrying container is able to provide refrigeration for the contents held within the internal volume of the container without the need for large mechanical refrigeration units or the use of previously frozen ice packs and the like.

13 Claims, 20 Drawing Sheets

PORTABLE, SUPERABSORBENT CARRYING CONTAINER ABLE TO PROVIDE REFRIGERATION FOR ITS CONTENTS ON-DEMAND

CROSS-REFERENCE

The present application is a Continuation-In-Part of Application Ser. No. 529,566 filed May 25, 1990, now pending, which is a Continuation-In-Part of Application Ser. No. 445,008 filed Dec. 4, 1989, now pending, which is a Continuation-In-Part of Application Ser. No. 142,077 filed Jan. 11, 1988, now U.S. Pat. No. 4,885,000 issued Dec. 5, 1989, which was a Continuation-In-Part of Application Ser. No. 001,648 filed Jan. 9, 1987, abandoned.

RESEARCH SUPPORT

The research for the present invention was supported by the Beth Israel Hospital Association.

FIELD OF THE INVENTION

The present invention is concerned generally with improvements in carrying containers constructed to protect their contents from the environment at large; and is particularly directed to improvements in superabsorbent carrying containers for the transport of deceased humans and/or animals and which are able to provide refrigeration on-demand for its contents.

BACKGROUND OF THE INVENTION

Carrying containers for the transport of one or more objects, large and small, have been known and used since the dawn of civilized man. Commonplace hand-held carrying devices include briefcases, suitcases, and shopping bags of various sizes and shapes which are composed of materials ranging from the fragile and biodegradable to the tough and impervious. However useful these many varieties of carrying containers may be, very few of them have been designed to withstand the effects of the general environment—that is, the impact of moisture, heat, microbes, and chemical contaminants and pollutants present in our air, water, and soil. In consequence, and in recognition of the fact that many items such as food and beverages fit for human consumption must be protected from the environment at large in order to avoid spoilage and/or contamination, an entire class of containers and devices have come into existence especially for this purpose.

In the main, this container class has employed methods for the artificial production of cold for food preservation purposes —more commonly known as "refrigeration." While blocks of ice were first used to freeze or chill the food and beverages to avoid spoilage and/or their chemical breakdown, the innovation of the 20th century has provided us with refrigerators, a machine or plant by which mechanical or heat energy is utilized to produce and maintain a low temperature; and concommitantly developed an entire technology directed towards refrigerants— substances suitable for use as working agents in a refrigerator— such as ammonia, sulphur dioxide, methyl chloride, and the now prevalent "Freons" or chloro-fluoro-methanes of various formulation. Refrigeration commonly occurs mechanically by compressing a vaporized refrigerant; condensing it by cooling; and throttling to the original pressure, when the refrigerant absorbs latent heat at a low temperature. Although a variety of transportable refrigeration units are known including refrigeration trucks and other vehicles, refrigerated railroad cars, as well as portable air conditioning units for cars, homes, and offices—refrigeration units are not usually employed as carrying containers in view of their size, bulk, and energy requirements.

In contrast, a variety of portable carrying containers having a short term cooling capacity have been developed for both consumer and industrial use. These typically take form as insulated containers into which periodically are placed a prepared cooling agent such as frozen blocks of ice, dry ice, and the now familiar plasticized packages of liquid which are first frozen in an immobile refrigerator repeatedly for use on more than one occasion. The carrying containers commonly take form as picnic baskets, insulated beverage jugs and bottles, and the like. Almost all of these are consumer-oriented products and are intended for the preservation of food and beverages for very short time periods.

A variety of other insulated or temperature controlled articles are known. Some are represented by U.S. Pat. Nos. 4,357,809; 4,745,909; and 4,742,958. Other items are described by Japanese Patent Publication Nos. 631140273 (880611); 59155486 (840904); and 55164278 (801220). These articles are merely illustrative of the developments in portable carrying containers which are able to provide some cooling or thermal insulating capacity for a short duration.

In contrast to the development of immobile mechanical refrigeration units and the introduction of small food and beverage containers intended for the consuming public which require the use of prefrozen ice in one form or another, there has been neither recognition nor appreciation of the longanimal standing analogous but unresolved situation and problems which continually arise after the occurrence of fatal human traumas, whether by injury or disease. Although it it perhaps unpopular to be reminded of the fact, it is indisuputable that human and aminal deaths occur continually from a variety of different causes and sources. One major cause is vehicular accidents on the highway from Which the death toll seemingly increases each year. Other human and animal deaths occur through catastrophic events caused both by nature and human intervention. Natural disasters include floods, earthquakes, hurricanes, typhoons, volcanic eruptions, and other naturally occurring cataclysmic events. In contrast, human involved disasters include airplane crashes, fires of dwellings and industrial sites, ship collisions, train crashes and other railroad failures, and military engagements and conflicts ranging from a very few to many millions of men.

Curiously, these catastrophic situations and events commonly share several attributes and features regardless of whether they were caused by nature or by human intervention. All too frequently, the loss of human and/or animal life occurs in a relatively remote geographical area or region, often at substantial distances from the nearest useable highway, airport, town, or city. Sometimes even reaching the disaster area is a major obstacle for the emergency medical personnel and other disaster relief teams because of the inaccessible nature of the terrain, the inhospitable climate, and the absence of roads, paths, or even trails into the disaster site. Unless the incident has occurred near a major town or city, it may require many hours to determine how best to reach the disaster area; and sometimes even several days pass before any meaningful amount of emergency equipment can be brought to the disaster site. In extreme situations such as an aircraft crash in a jungle or mountainside where only an air-lift system of transport can conceivably be employed to supply the emergency rescue teams of eight or ten persons who set out on foot, the recovery of human remains can sometimes take up to a week or more to achieve.

It will be recognized and appreciated that a human corpse or animal body lying exposed to the elements and the environment at large for even several hours will begin to decompose and degenerate such that the remains are often unrecognizable and unidentifiable by the time the rescue teams arrive. The common practice in this post-Vietnam conflict era is for the attending rescue personnel to bring containers for each of the dead as part of the subsequent transport and final disposition of the remains These containers typically are large sacks formed of flexible, resilient material such as nylon; and are fitted with water-tight closures such that the internal contents will remain within the interior of the container. Such personnel containers have been dubbed "body bags" and serve as nothing more than protective shells by which to insulate the emergency attending personnel and rescue teams from the decomposing and deteriorating tissues and organs resting within the container for the entirety of the time required for transport and relocation of the remains to an autopsy room for medical evaluation by a pathology team; to a morgue; or subsequently to a funeral director for final disposition It will be apparent even to the inexperienced that a major, recurring problem in such catastrophic disaster situations involving human and/or animal deaths is the general inability to prevent the decomposition and destruction of the tissues and organs of the corpse for many days even after the bodies have been found at the site of the disaster From the moment of the catastrophic event causing death, the body remains lie exposed to air, heat, microbes, moisture, and the environment at large; as well as to the internal process of biological decay caused and typified by the onset of rigor mortis. Hours, if not days, will pass until the rescue teams and personnel even arrive at the disaster site. Afterwards, the remains are placed in a closed bag which cannot protect its internal contents from exposure to heat and microbes; and which allows the process of decay to continue rapidly within the interior of the bag. During their time of transport within the bag, the remains continue to decompose, and undergo putrefaction causing much release of fluids and a substantial retention of gases in the body; this in consequence increases the rate of tissue destruction and causes a major distortion of body size and identifiable features in the remains. Not until a central receiving area is reached where trucks or other refrigeration can be obtained, is there any meaningful decrease or reduction in the rate of tissue decay and deterioration. In many instances, much if not all of the corpse has degenerated into an unidentifiable mass of comingled fluids and tissues making the identification of the person, such less the exact cause of his death, difficult if not almost impossible.

In addition, if the person or animal had died under suspicious circumstances; or had been infected with a contagious disease agent; or if the cause of death is unknown; the deterioration of the body remains poses a major and sometimes overwhelming problem for the pathologist and for any forensic investigations to come. All too often, by the time the remains reach the pathologist, the corpse itself is a potent source of infection and contamination for the attending personnel and poses a major risk and hazard and for all persons then coming into contact with the contents of the carrying container. The subsequent problems for the funeral direction and for final disposition of the remains then become almost insurmountable. Cremation becomes the standard means for final disposition, often against the wishes of the immediate family and other concerned persons, because of the risk of exposure and potention infection caused by the deteriorating and decaying corpse lying in the interior of the container.

It is clear that a major improvement and benefit would result if it were possible for the emergency rescue personnel reaching a disaster site to bring with them a portable carrying container which could absorb at least some of the fluids released by the corpse after placement within the container for the time required until a central facility with refrigeration services is available. In addition, it would be far more preferable were a carrying container able to provide refrigeration on-site and on-demand for its contents in such catastrophic event situations because the rate of decay and tissue destruction would then be meaningfully retarded. Insofar as is presently known, however, there have been no developments nor improvements of carrying containers suitable for the transport of human and animal remains beyond the conventionally known body bag design.

SUMMARY OF THE INVENTION

The present invention provides a portable, superabsorbent carrying container able to provide refrigeration for its contents on-demand. One embodiment of the carrying container comprises:

a portable, closed container comprising at least one wall and having a determinable internal volume and spatial configuration;

at least one superabsorbent fibrous lining disposed within the internal volume of the closed container;

means for inserting and removing an object from the spatial volume provided by the superabsorbent fibrous lining within the closed container;

first on-demand means in communication with the internal volume of the closed container for introducing a freezible liquid to the superabsorbent fibrous lining on-demand, such freezible liquid as is introduced via the first on-demand means being absorbed by the superabsorbent fibrous lining; and second on-demand means in communication with the internnal volume of the closed container for introducing a refrigerant gas to the superabsorbent fibrous lining on-demand, such refrigerant gas as is introduced via the second on-demand means causing the freezing of such liquids as have been absorbed by the superabsorbent fibrous lining.

An alternative embodiment of the superabsorbent carrying container able to provide refrigeration for its contents ondemand comprises:

a portable, closed container comprising at least one wall and having a determinable internal volume and spatial configuration;

at least one superabsorbent fibrous lining disposed within the internal volume of the closed container;

a freezible solid coating applied to at least a portion of the superabsorbent fibrous lining within the closed container;

means for inserting and removing an object from the spatial volume provided by the coated superabsorbent fibrous lining within the closed container; and on-demand means in communication with the internal volume of the closed container for introducing a refrigerant gas to the coated superabsorbent fibrous lining on-demand, such refrigerant gas as is introduced via the on-demand means causing the freezing of the solid coating of the superabsorbent fibrous lining.

DETAILED DESCRIPTION OF THE FIGURES

The present invention may be more easily and completely understood when taken in conjunction with the accompanying drawing, in which.

DETAILED DESCRIPTION OF THE PREFERRED EMBODIMENTS

Figure 1B:
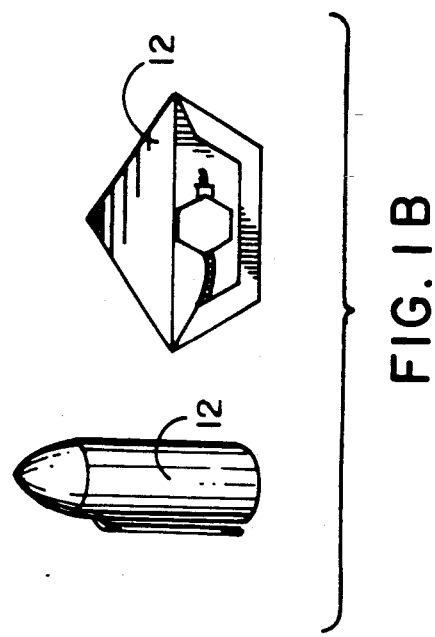
FIGS. 1a and 1b illustrate the present invention in combination with other equipment useful in the performance of the invention.

The present invention is a portable and disposable, superabsorbent carrying container able to provide refrigeration on-demand for its contents. The superabsorbent carrying container can be constructed in a variety of different ways to meet and to accommodate diverse uses and applications. For these reasons, it is expected that the configurations, dimensions, volumes, surface areas, mode of construction, materials employed, and intended manner of use will be different and variable for each embodiment. Accordingly, although the three different preferred embodiments disclosed by the figures and the descriptive text hereinafter are directed to superabsorbent carrying containers intended for use as personnel or body bags for the containment of human and/or animal corpses, it will be recognized via the variety of constructions that the range of intended applications are diverse, multiple, and unrelated.

By the broadest definition of the present invention, the portable and disposable, superabsorbent carrying container able to provide refrigeration on-demand comprises a closed container having at least one wall as well as a determinable internal volume and identifiable spatial configuration. Disposed within the internal volume of this closed container is at least one superabsorbent fibrous lining which is preferrably in substantial alignment with the wall and the spatial configuration of the closed container. For purposes of entry and egress from the lined closed container, means are present for inserting and removing an object from the spatial volume provided by the superabsorbent fibrous lining within the closed container. Each embodiment of the present invention also comprises on-demand means in communication with the internal volume of the closed container for the purpose of introducing a refrigerant gas to the superabsorbent fibrous lining on-demand, the introduction of such refrigerant gas via these on-demand means causing the freezing of such liquids or solids as are present on or within the superabsorbent fibrous lining.

There is, however, one requisite feature which is variable within the different embodiments and definitions of the present invention. The requirement, in the alternative, therefore is: on-demand means in communication with the internal volume of the closed container for introducing a freezible liquid to the superabsorbent fibrous lining on-demand, such freezible liquid as is introduced via these on-demand means being absorbed by the superabsorbent fibrous lining within the closed container. Alternatively, a freezible solid coating has been applied to at least a portion of the superabsorbent fibrous lining within the closed container. By either format, the introduction and consequence of the refrigerant gas to either the liquid absorbed by the superabsorbent fibrous lining or the presence of the solid coating on the superabsorbent fibrous lining causes the freezing of these materials into a frozen mass which provides refrigeration on-demand for the contents of the closed carrying container.

Each embodiment of the portable, superabsorbent carrying container able to provide refrigeration on-demand for its contents is intended to be constructed in advance; can be carried and transported as a discrete article in a prepackaged rolled or folded form or as an unpackaged open/bolt form; and can be prepared in either a pre-sterilized or a non-sterilized state. Upon reaching the intended site of use and/or application, the superabsorbent carrying container will serve effectively in the desired setting; and act as a superabsorbent, refrigerated container to protect and preserve the human and/or animal remains or other objects placed within the internal volume of the container. Once the corpse or other object is held within the closed container and the refrigeration capability employed to cool and preserve the internal contents, the entirety of the carrying container may then be removed as a discrete article to a central receiving area, morgue, pathology department of a hospital, or any other location without fear of major deterioration and destruction of the internal contents; and without risk of exposing any person to accidental infection or contamination from the potentially hazardous fluids and liquids released by the internal contents during the transportation process.

It will therefore be recognized and appreciated that the present invention provides multiple, major, and unique benefits and advantages which were not previously known or available by conventionally used carrying containers. These include:

1. The present superabsorbent carrying container is easily portable, durable, and provides refrigeration on-demand for the contents placed within it. The superabsorbent carrying container can be configured, dimensioned, and constructed to serve many different functions and uses under a wide variety of different locations, settings, and circumstances. While one preferred use and application is as a personnel bag for the removal, transport, and containment of human and/or animal body remains after death, many non-medical applications are intended. Among the diverse functions and applications are the following: as refrigerated packaging and shipping containers for edible meats, carcasses, and edible delicasies which deteriorate quickly in heat; as substitute coolers and beverage containers used by the consuming public as picnic and beverage baskets and packages; and as packaging containers for explosives and other highly volatile chemicals and products which become dangerous when heated or which tend to release fluids when exposed to the environment at large.

2. The present invention is a superabsorbent carrying container comprising a fibrous lining able to absorb at least 15 times and preferrably up to 50 times its own weight in fluids. In some embodiments, the superabsorbent fibrous lining is constructed as a multi-laminate sheet which can optionally be detached and replaced at will by another similarly sized laminated sheet cut from a prepared roll or bolt as needed. In this manner, the superabsorbent fibrous lining of the carrying container can—at one's option and choice—be easily substituted and replaced by another similarly configured and dimensioned lining without discarding or disposing of the other parts of the carrying container forming the present invention as a whole.

3. The superabsorbent carrying container able to provide refrigeration on-demand for its contents not only protects and preserves the objects placed within the internal volume of the container from deterioration and spoilage but also absorbs such liquids as are released by the object from the moment the object is positioned within the container itself—with or without refrigeration. The carrying container will continue to absorb all fluids released by the object during the entirety of the time the object is held within the carrying container and regardless of whether the object is refrigerated or not. Upon reaching the intended destination, the carrying container is then opened and the internalized object removed for further disposition. The used carrying container—then containing and holding the abssorbed fluids and other liquids released by the object or otherwise absorbed by accidental or inadvertent contact—will not drip, flow, or otherwise release any of the absorbed fluid over the entirety of the volume or perimeter of the carrying container itself. The used carrying container, now containing substantial quantities of fluid and/or other liquid wastes, may nevertheless be folded or rolled into a selfcontained format; and then be discarded or destroyed completely as a single unitary article without danger of accidental contamination or spillage from the absorbed contents.

PREFERRED EMBODIMENTS

Some preferred embodiments of the present invention are described in detail hereinafter and are illustrated via FIGS. 1-22 inclusive. For purposes of providing a more focused and clear disclosure, the majority of the detailed description presented hereinafter is intentionally directed to those preferred embodiments of a carrying container suitable for use in the removal and transportation of human and/or animal corpses or body remains after fatal trauma and death. It will be explicitly recognized and understood, however, that this directed description is provided merely for illustrative purposes only; and that the present invention is not to be limited or restricted in any manner, form, or usage to the constructions, materials, or applications described hereinafter. The preferred embodiments are only illustrative examples directed to the construction of personnel bags because it is expected that this will be one major area of use and application for the present invention. Nevertheless, because of the expected and intended diversity and range of applications beyond the removal and transport of human and/or animal remains, there is no basis or rationale whatsoever for presuming that the present invention is limited to only these applications and uses. With this understanding in mind, the individual preferred embodiments which are merely exemplary and representative of the subject matter as a whole which comprises the present invention will be described.

Figure 1A:
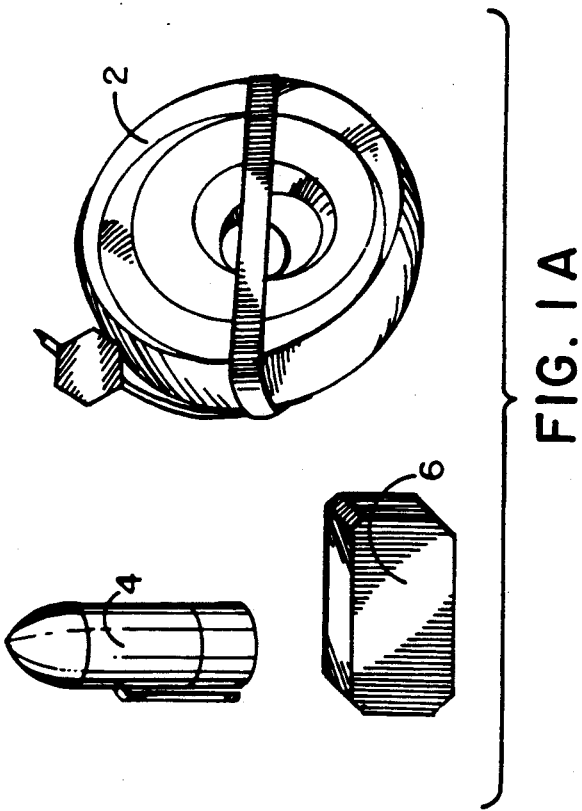

The portable nature of the superabsorbent carrying container able to provide refrigeration on-demand for its contents and its supporting equipment are illustrated by FIGS. 1a and 1b respectively, each of which illustrates a different embodiment of the invention. FIG. 1a illustrates the superabsorbent carrying container 2 in a rolled up, folded format ready for transport to the intended site of use. Positioned adjacenlty are a portable canister 4 of a refrigerant gas and a portable reservoir 6 containing a freezible liquid. This embodiment 2 of the superabsorbent carrying container is constructed to comprise on-demand means for introducing a freezible liquid to the internal volume of the container; for this reason, it is desirable, but not absolutely required, that the reservoir 6 of a freezible liquid be carried by the intended user to the geographical location along with the carrying container 2 and the pressurized canister 4 of a refrigerant gas. In the alternative, any freezible liquid which may be obtained at the intended place of use or application and be introduced as such to the internal volume of the superabsorbent carrying container 2 may be substituted at will. The reservoir 6 of a freezible liquid is thus an optional adjunct item rather than an essential requirement.

In contrast, another embodiment of the invention is illustrated by FIG. 1b which shows a superabsorbent carrying container 10 in a folded/bundled form and another portable canister 12 of a refrigerant gas. This embodiment 10 of the superabsorbent carrying container does not require the introduction of a freezible liquid into the internal volume of the container because it has been constructed in advance with a freezible solid coating applied to at least a portion of the superabsorbent fibrous lining of the container.

In addition, the pressurized canister 12 of a refrigerant gas is also merely a desirable adjunct to the superabsorbent carrying container 10. The canister 12 is purposely designed to be both portable and prepared in advance in order to provide convenience as well as use at a remote geographic location. However, a refrigerant gas obtainable at the intended site of use or application may be substituted at will.

A FIRST PREFERRED EMBODIMENT

Figure 2:
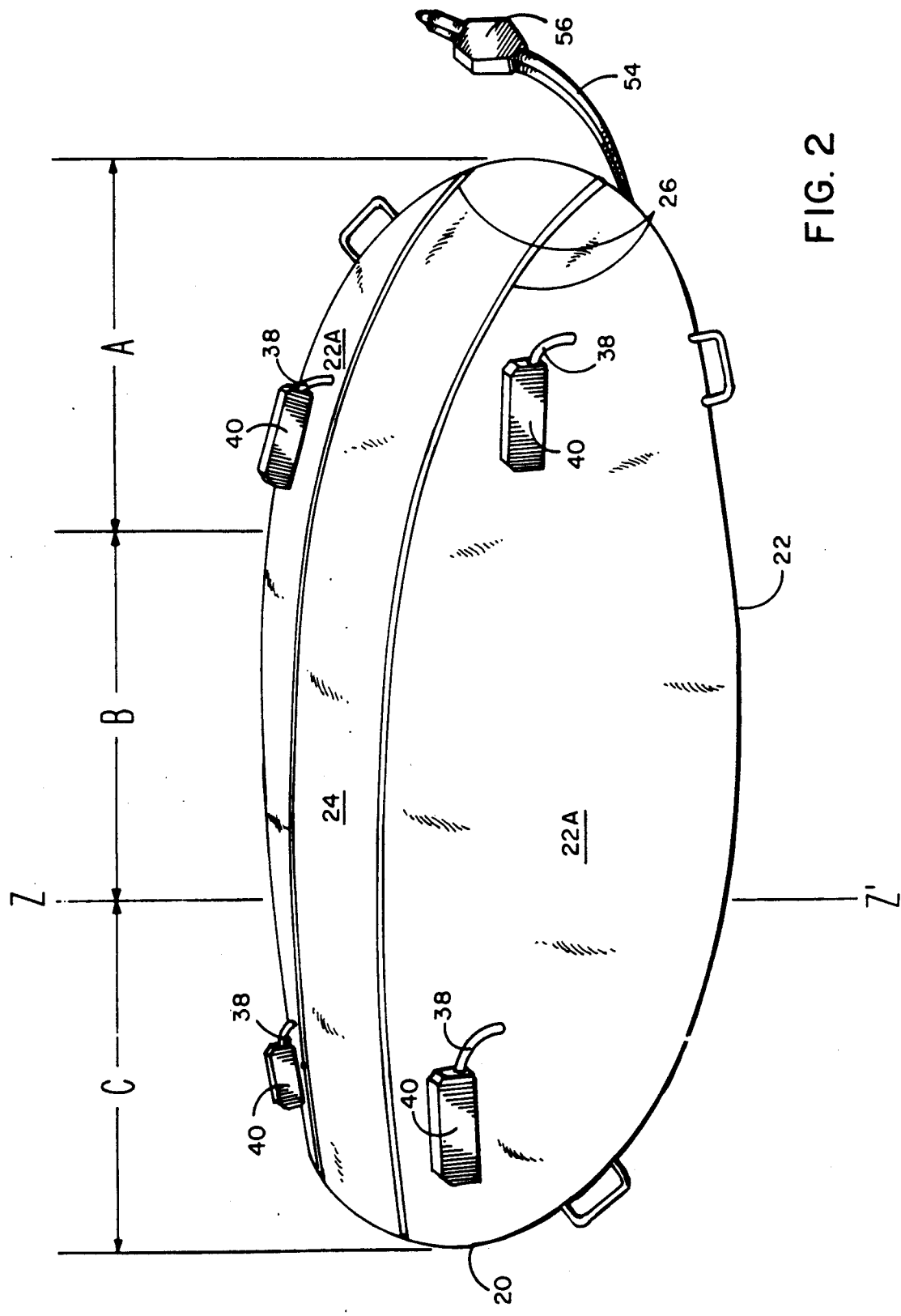
FIG. 2 is a perspective view of a first preferred embodiment of the carrying container ready to perform its intended function.
Figure 3:
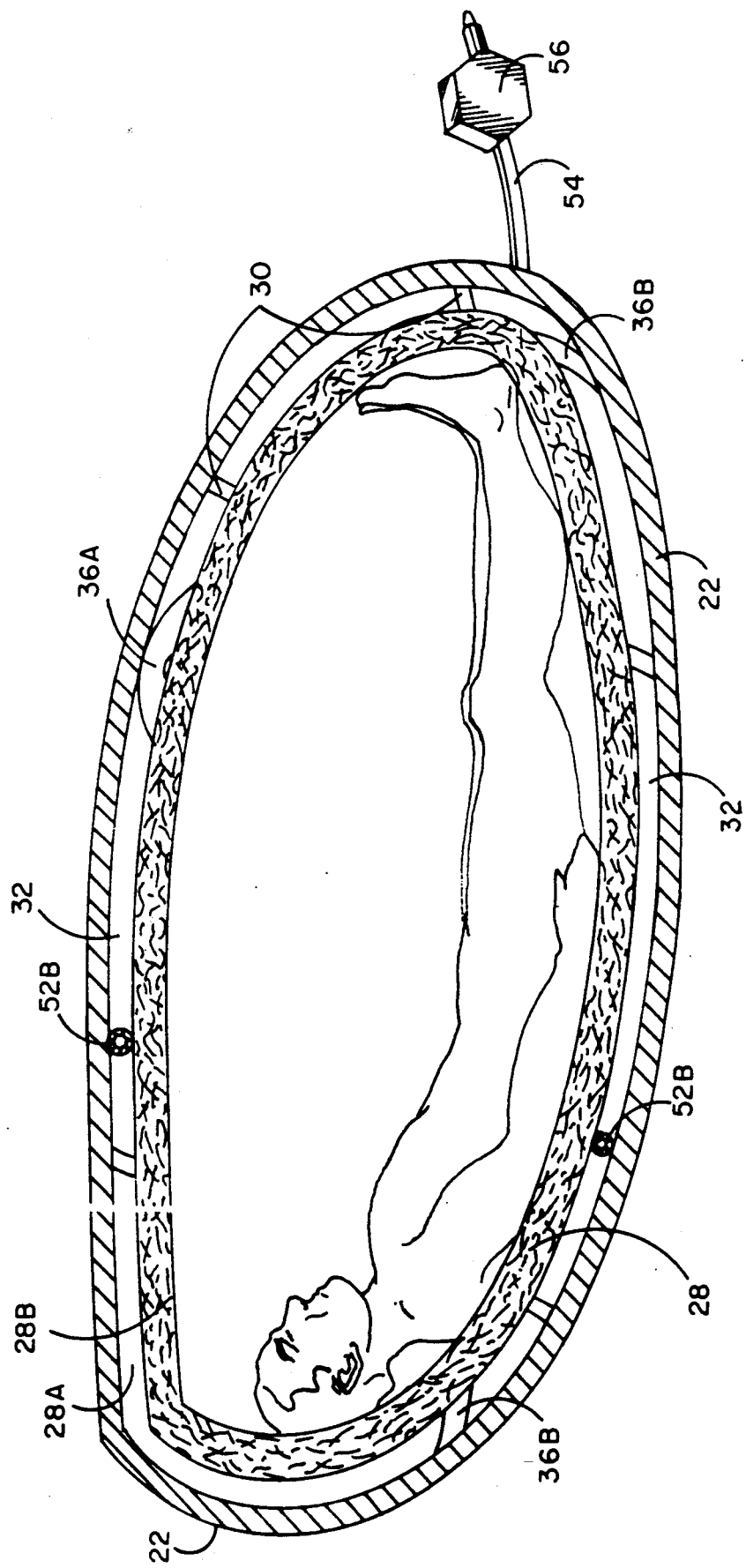
FIG. 3 is a cross-sectional view of the carrying container illustrated within FIG. 2.
Figure 4:
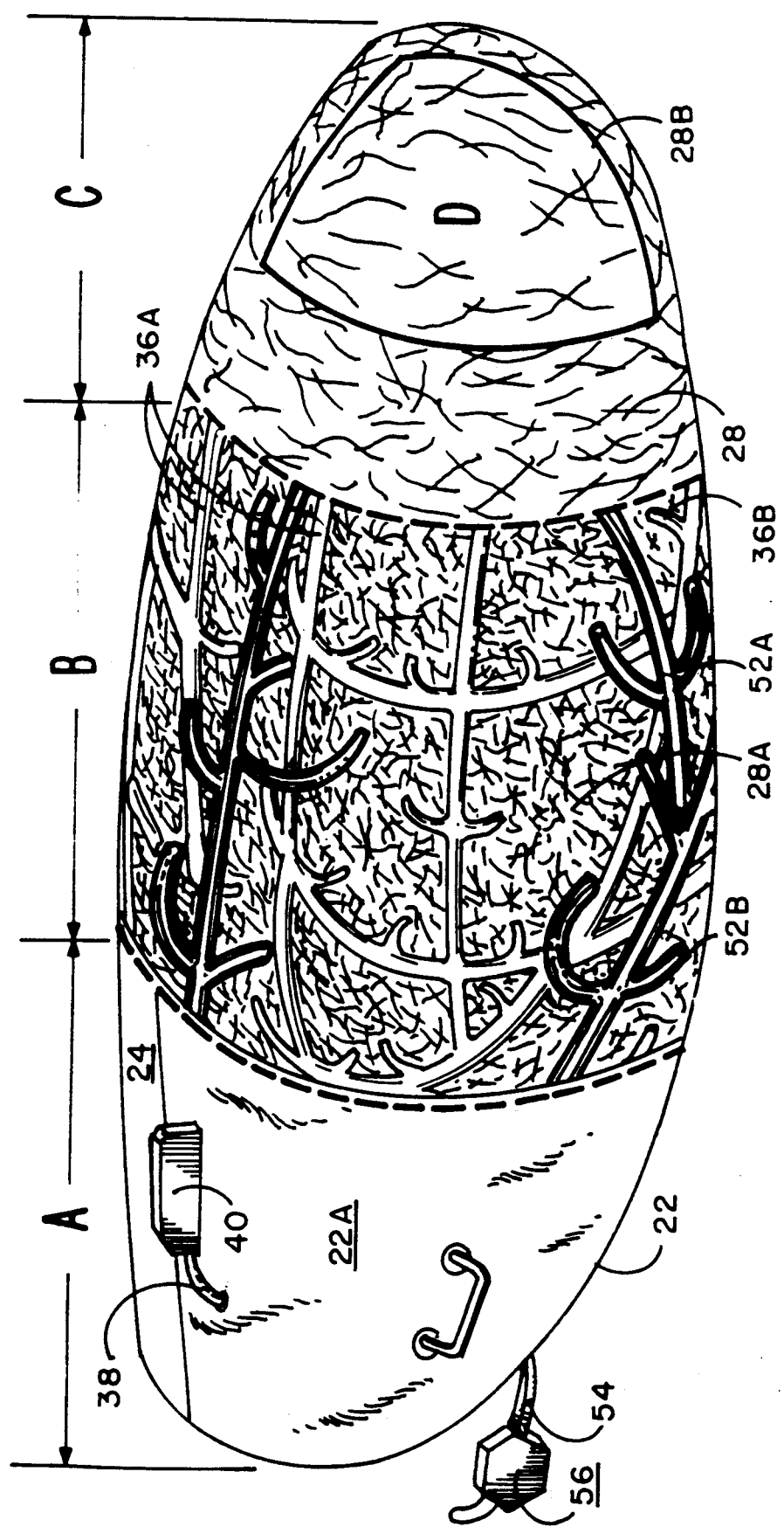
FIG. 4 is a break-away perspective view of the first preferred embodiment illustrated by FIG. 2.
Figure 5:
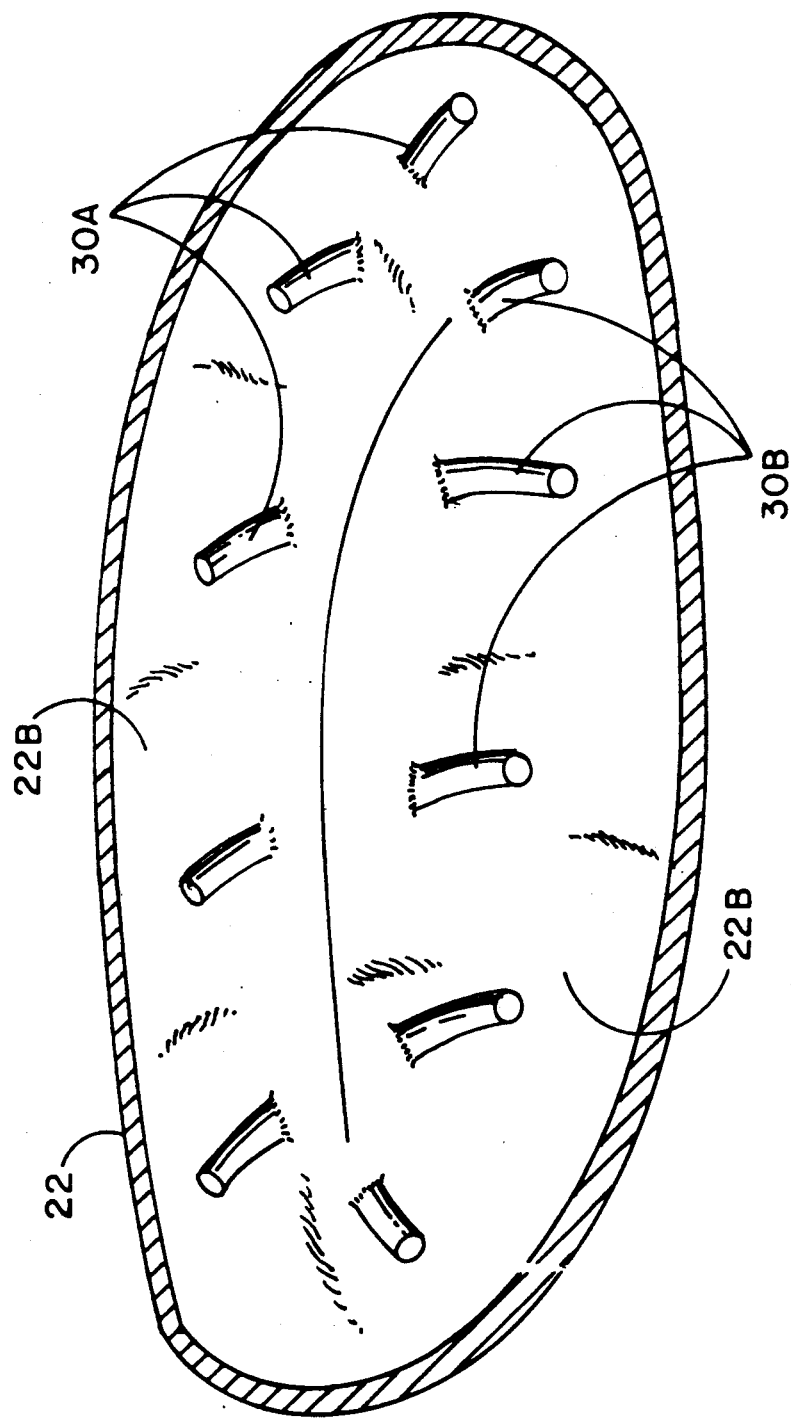
FIG. 5 is a view of the under-surface of the external shell for the embodiment illustrated by FIG. 2.
Figure 6:
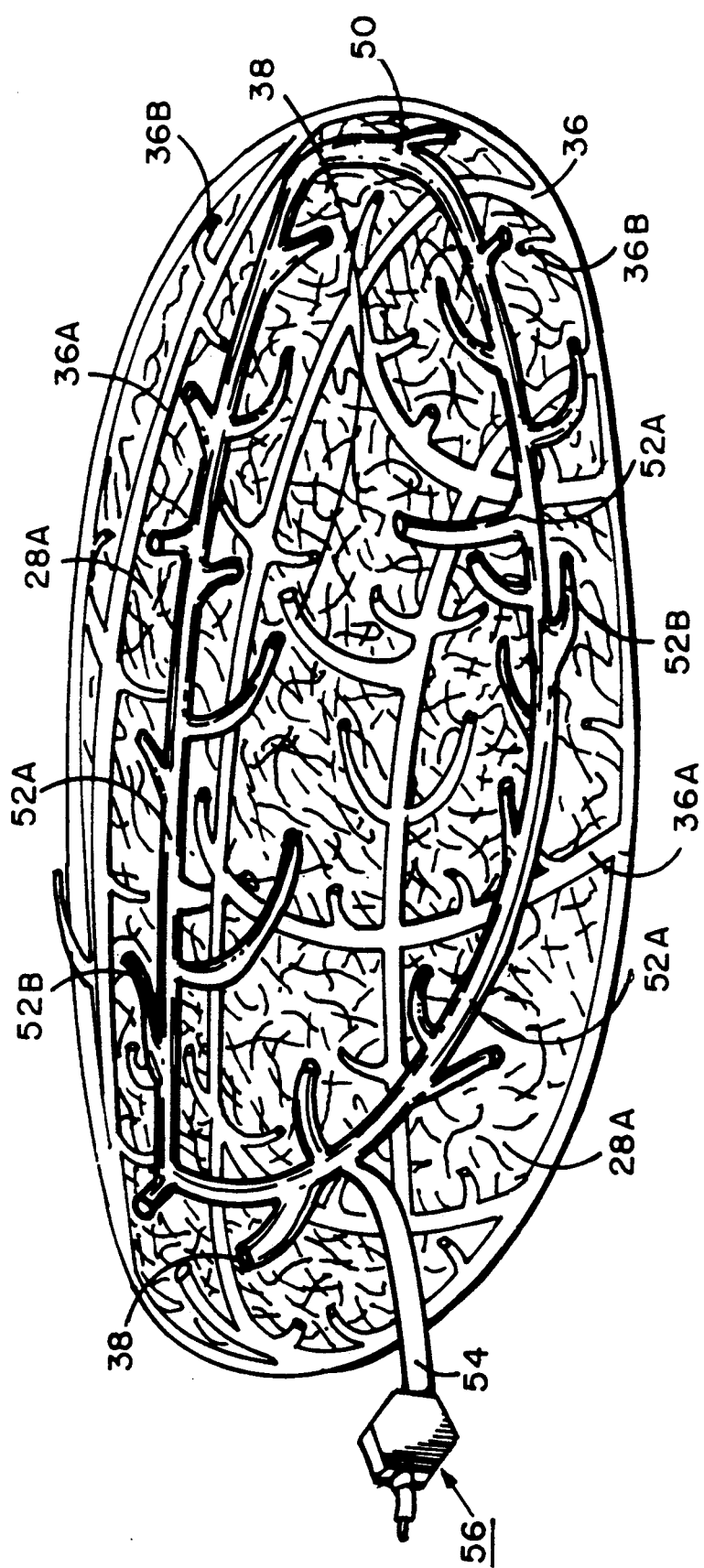
FIG. 6 is a perspective view of the carrying container of FIG. 2 with the exterior shell removed.
Figure 7:
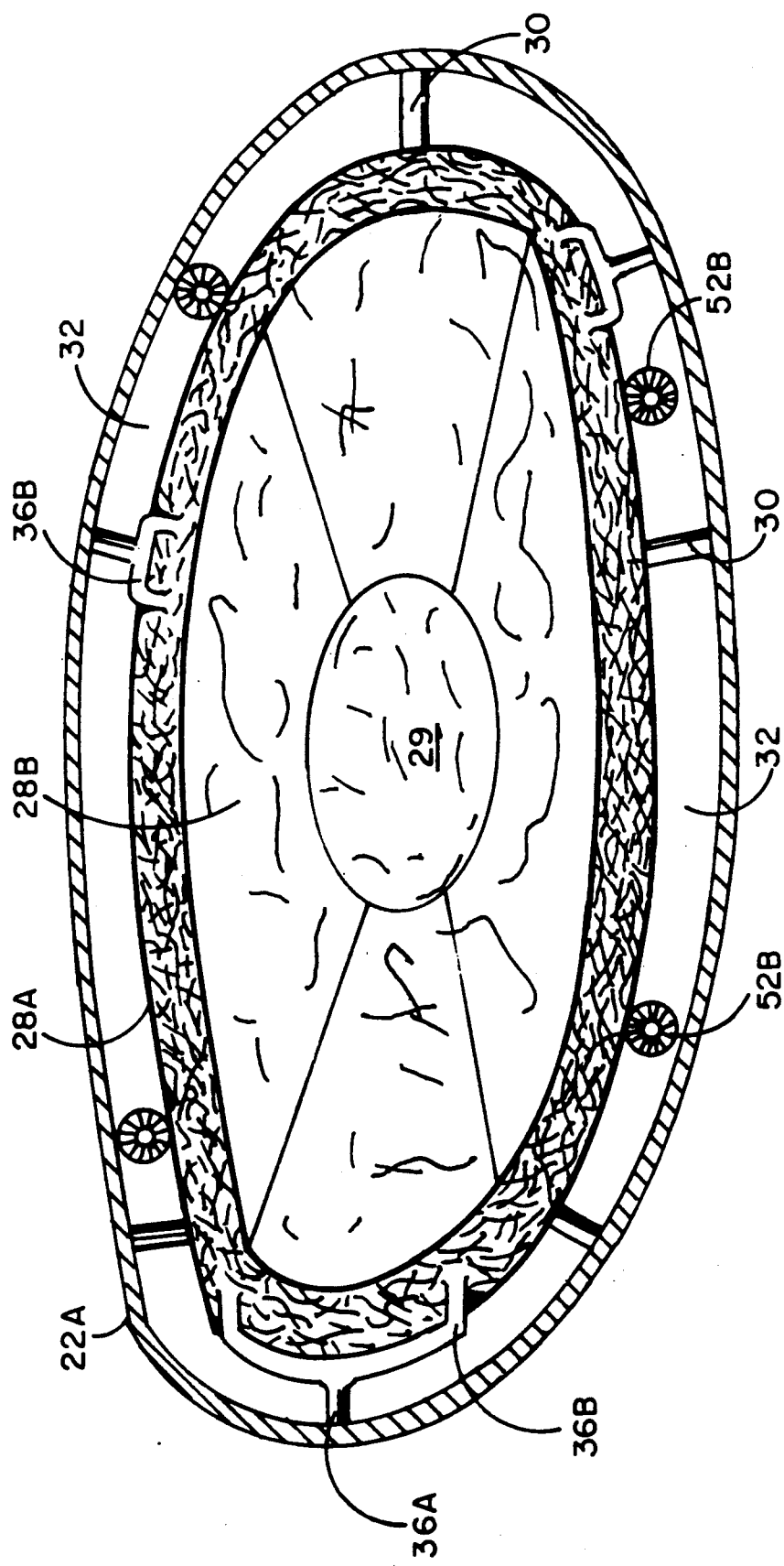
FIG. 7 is a cross-sectional view of the carrying container of FIG. 2 along the axis zz'.

A first preferred embodiment of the superabsorbent carrying container able to provide refrigeration on-demand for its contents is illustrated by FIGS. 2-7 respectively. FIGS. 2 and 4 provide perspective overhead views of the first preferred embodiment as a whole and in a break-away view showing the various component parts in a layered format; FIGS. 3 and 7 show longitudinal and transverse cross-sectional views of this first preferred embodiment; and FIGS. 2, 5, and 6 illustrate the various layers and construction design of the first preferred embodiment in alternate perspective views. It will be recognized and appreciated therefore that FIGS. 2-7 inclusive represent the entirety of this first preferred embodiment in alternate views in an effort to clearly illustrate the construction and design of this specific embodiment.

As appears particularly in FIGS. 2-4 inclusive, there appears the superabsorbent carrying container 20 designed and constructed for use in holding and transporting a human corpse from the site originally found to another destination. The superabsorbent carrying container is illustrated as divided into zones A, B, and C for clarity, with D indicating the internal spatial volume of the carrying container; is configured in substantially oval form; and is dimensioned to accommodate a corpse of any weight and length up to about 7 feet. The carrying container 20 is comprised of an outer shell 22 which is desirably composed of flexible, durable, and fluid-impermeable material. The outer shell 22 is formed as one wall and provides a closed container having a determinable internal volume and spatial configuration. A closure flap 24 is constructed as a component part of the shell wall 22 and contains a fluid-tight closure 26 which allows the outer shell 22 to be closed and sealed securely on-demand. The closure flap 24 and the closure 26 in combination provide the means for inserting and removing an object (such as a human corpse) from the spatial volume of the closed carrying container 20.

As is seen via FIGS. 3, 4, and 7, there is at least one superabsorbent fibrous lining 28 disposed within the internal volume of the closed container 20. In this embodiment, the superabsorbent fibrous lining is in substantial alignment with the shell wall 22 and the spatial configuration of the carrying container 20. As seen in FIGS. 5 and 7, the underside or interior surface 22b of the shell, optionally but desirably, has a plurality of flexible spacing fingers 30 extending radially inward into the internal volume 29 of the closed container 20. While the proximal end 30a is preferrably permanently joined to the outer shell 22, the distal end 30b of each spacing finger 30 flexibly extends and freely abutts the external surface 28a of the superabsorbent fibrous lining 28. In this manner, an internal spacing zone 32 is created which, although irregular in configuration and variable in volume due to the flexible nature of the spacing fingers 30, nevertheless provides an open passageway or corridor between the outer shell 22 and the superabsorbent fibrous lining 28.

As appears in FIGS. 3, 4, 6, and 7, positioned within the internal spacing zone 32 are: first on-demand means for introducing a freezible liquid to the superabsorbent fibrous lining 28; and second on-demand means for introducing a refrigerant gas to the superabsorbent fibrous lining 28. Each of these are desirably positioned throughout the length and volume of the internal spacing zone 32; each is in direct physical contact with the superabsorbent fibrous lining 28 at multiple points; each is constructed to extend through the outer shell 22 of the carrying container 20; and each is in fluid communication with an individual source of a freezible liquid or a refrigerant gas as required.

The on-demand means for introducing a freezible liquid to the superabsorbent fibrous lining takes form in this first preferred embodiment as a conduit system 34 which is constructed internally as a system of major and minor flow tubes 36. As seen in FIGS. 4 and 6, the conduit system 34 also includes a series of connecting hoses 38, each of which is in flow communication with a reservoir 40 containing a freezible liquid 42. The reservoirs 40 are individually positioned on the outer surface 22a of the outer shell 22 as appears in FIGS. 2 and 4. When desired or required, the freezible liquid 42 is released from the reservoirs 40 and flows through the connecting hoses 38 into the flow tubes 36. The major tubes 36a serve as the major internal arteries of the conduit system and bring the freezible liquid into proximity with the external surface 28a of the superabsorbent fibrous lining 28. The minor tubes 36b are open ended at their distal ends and are in intimate contact with the external surface 28a of the superabsorbent fibrous lining 28. Accordingly, when the freezible liquid initially held within the reservoirs 40 until required is released on-demand, it flows through the connecting hoses 38 extending through the outer shell 22 and through the conduit system 34 positioned within the internal spacing zone 32 such that the major tubes 36a and then the minor tubes 36b convey the freezible liquid to the superabsorbent fibrous lining 28 where the entirety of the freezible liquid is completely absorbed.

Concurrently, the second on-demand means for introducing a refrigerant gas to the superabsorbent fibrous lining on-demand is provided by a refrigerant gas channeling system 50 which provides a system of gas piping 52 formed as major pipes 52a and minor pipes 52b respectively. The channelled system of gas piping 52 positioned within the internal spacing zone 32 is in flow communication with a gas main 54 which extends through the outer shell 22 and is preferrably constructed to have a gas regulation valve 56 at its distal end. The gas main 54 and gas regulation valve 56 are configured and intended to be attached to a source of a refrigerant gas 58; and such refrigerant gas as is introduced via the regulation valve 56 through the gas main 54 into the system of gas piping 52 is then carried by the major pipes 52a and then by the minor pipes 52b for release adjacent to the external surface 28a of the superabsorbent fibrous lining 28. In this manner, such refrigerant gas as is introduced ondemand via the gas channeling system 50 will cause the freezing of such liquids as have been absorbed previously by the superabsorbent fibrous lining 28.

In the expected manner of use, a corpse will be placed into the spatial volume 29 provided by the superabsorbent fibrous lining 28 within the closed container 20. The closure flap 24 allows the corpse to be placed internally and then sealed using the fluid-tight closure 26 to provide a complete seal of the outer shell 22. The reservoirs 40, each holding a freezible liquid 42, are individually joined to the connecting hoses 38; and the flow of the freezible liquid begins through the conduit system 34 to the superabsorbent fibrous lining 28. All the freezible liquid introduced via the conduit system 34 becomes absorbed by the superabsorbent fibrous lining 28. In addition, any and all fluids and other liquids released by the corpse resting within the interior of the carrying container 20 are also continuously absorbed by the superabsorbent fibrous lining 28 which encompasses and surrounds the corpse as a capsule. Subsequently, a refrigerant gas 58 is introduced from its source and is channeled through the regulation valve 56 through the gas main 54 into the channel system of gas piping 52. The major pipes 52a and the minor pipes 52b channel the refrigerant gas to the absorbent fibrous lining. In consequence, such refrigerant gas as is introduced via the gas channeling system 50 will cause the freezing of all liquids which have been previously absorbed by the superabsorbent fibrous lining 28. In this manner, the carrying container 20 is able to provide refrigeration on-demand for its contents.

CHARACTERISTICS, PROPERTIES, AND FEATURES OF THE REQUISITE COMPONENTS COMPRISING THE PRESENT INVENTION

The Closed Container

The carrying container should comprise at least one wall, although it may have several discrete and identifiable walls in alternate constructions and embodiments; have a determinable internal volume and spatial configuration; and provide means for inserting and removing an object from the internal volume of the container itself. It is highly desirable that the materials used to construct the outer shell of the carrying container be fluid-impermeable, flexible, and pressure resistant. Alternatively, less desirable embodiments will be constructed with inflexible walls; be permeable to fluids (gases and liquids); and have a minimum of resistance to pressure. Accordingly, the preferred materials for use are the conventionally known olefins and organic polymers such as nylons, polyesters, polyacrylamides, polyethylenes, polypropylenes, and the like which provide both flexibility and durability for the outer shell. In general, however, almost any material may be employed to construct the outer shell of the carrying container in accordance with the present invention.

The means for inserting and removing an object from the spatial volume provided by the outer shell and the superabsorbent fibrous lining disposed within the shell can take any conventionally known form or mode of construction. It is most desirable that the outer shell be provided with fluid-tight closures which may be opened and closed repeatedly as desired and which will provide a fluid-tight seal when closed. Many means of construction and closure are available commonly and any of these may be employed at will for use with the present invention. It is expected that in preferred embodiments a combination of zippers and interlocking air-sealing fittings will be employed in combination as one of the better modes of construction to insure both a good closure and a fluid-tight seal on-demand. However, any other conventionally known closure is acceptable for use.

There is no limitation or restriction whatsoever as to the configuration of the carrying container, its dimensions, or its spatial configuration. Accordingly, the carrying containers may be round, oval, square, or irregular in shape; may be minute or huge in volume and carrying capacity; and its dimensions may extend from the hand-held size to a capacity which requires the efforts of several persons to lift and carry.

The Superabsorbent Fibrous Lining

Figure 8:
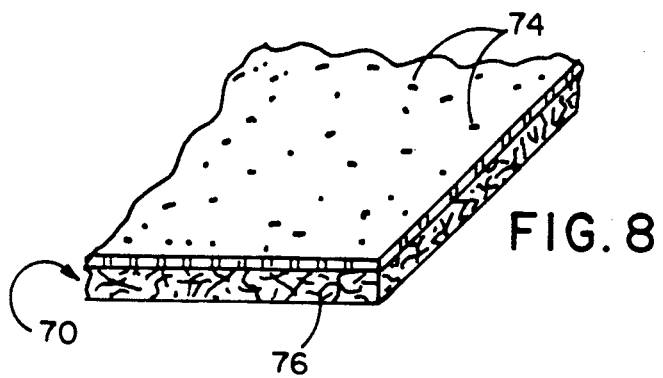
FIG. 8 is a perspective view illustrating a preferred two component laminated sheet construction comprising the superabsorbent fibrous lining of the embodiment illustrated within FIGS. 2–7 respectively.
Figure 9:
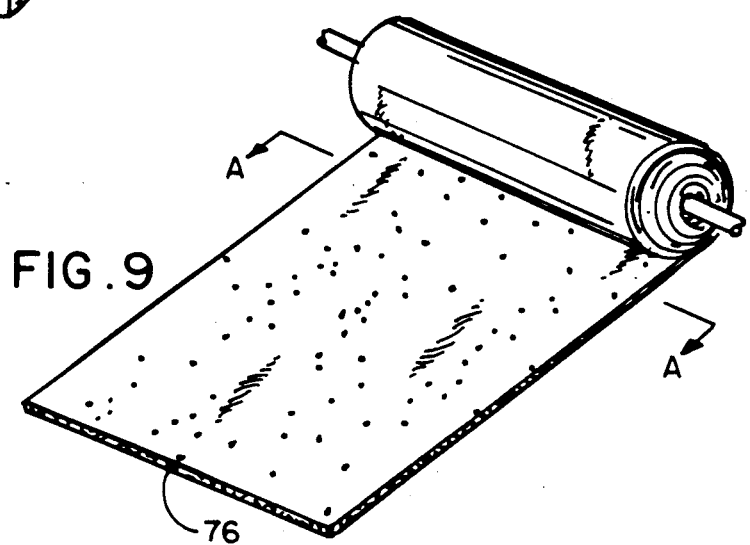
FIG. 9 is a perspective view of a prepared roll of the two component superabsorbent fibrous lining of FIG. 8.
Figure 10:
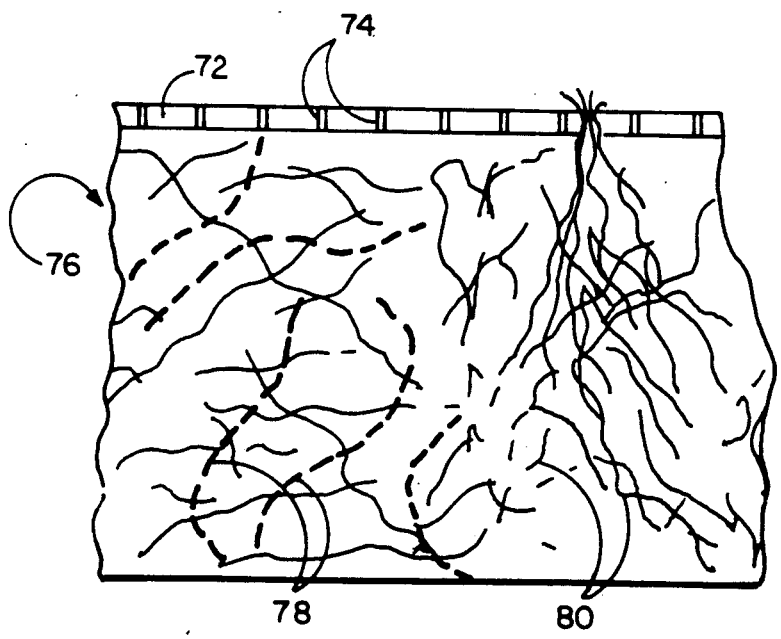
FIG. 10 is a detailed cross-sectional view of the two component superabsorbent fibrous lining of FIG. 8.

Details regarding the preferred superabsorbent fibrous lining are illustrated by FIGS. 8-10 respectively. FIG. 8 shows a perspective view of the superabsorbent fibrous lining as a laminated construction. As illustrated, the fibrous lining 70 is most desirably formed as a two-part laminated sheet comprising a fluid-permeable covering stratum 72 having representative pores 74 to indicate the fluid permeable nature of the covering. Underlying this fluid permeable covering stratum 74 is the superabsorbent fibrous layer 76 comprising fluid-absorbing fibers able to absorb at least 15 times their own weight of fluid. The preferred form and embodiment of these superabsorbent fibers is as a non-woven absorbent batt composed of a substantially uniform array of superabsorbent fibers 78 (able to absorb not less than 15 times their own weight of fluid) and support fibers 80. While the primary function of the superabsorbent fibers 78 is to absorb high volumes of fluid, the support fibers 80 interlock with the superabsorbent fibers to provide strength and stability for the superabsorbent fibrous batt both before and after it is saturated by fluid. The support fibers 80 also provide good absorbent and adsorbent qualities and offer good resiliency when either in wet or dry states. In general, the superabsorbent fibers 78 typically comprise between 5-50% of the total fiber content for the nonwoven absorbent batt.

The multi-laminate sheet construction preferred for use as the superabsorbent fibrous format may be manufactured and supplied in roll form as shown by FIG. 9. In keeping with the optional replaceable and disposable formats for the superabsorbent fibrous lining as described previously, FIG. 9 illustrates a roll of the preferred two-part constructed, superabsorbent laminated sheet—a specific dimensioned segment of which is removed by cutting along the line aa' as indicated. The newly cut segment would then be used as a substitute for the fibrous lining originally present within the internal volume of the closed carrying container.

It will be noted and appreciated that the preferred laminated construction for the superabsorbent fibrous lining as described herein is part of the subject matter described and claimed within copending patent application of Conrad A. D'Elia and John D. Hogan, entitled "Superabsorbent Non-woven Fibrous Material", the text of which is expressly incorporated by reference herein. In addition, the most preferred composition and blend of fiber materials to be described subsequently also comprises a major part of the above identified, copending patent application. Preferably, the superabsorbent fibers employed in the non-woven absorbent batt within the multi-laminate construction is a fiber formed from a blend of heterocyclic carbonate and a copolymer of maleic anhydride and isobutylene, as described in U.S. Pat. Nos. 4,616,063; 4,705,773; 4,731,067; 4,743,244; 4,788,237; and 4,813,945 respectively the text of which are also individually incorporated by reference herein for their disclosures.

For optimal absorptive function by the non-woven absorbent batt, the superabsorbent fibers are mixed with support fibers, preferably using several deniers of polyester. A variety of other materials and compositions may also be used for the support fibers themselves. These include: rayon, cotton, polypropylene, nylon, and polyethylene. These support fibers, regardless of specific composition or materials, should interlock with the superabsorbent fibers, preferrably in a nonwoven manner. In addition, although a great range of percentage content for the support fibers may be utilized, the percentage ratio of support fibers typically comprises 50-95% of the total fiber content for the absorbent batt.

The fluid absorption characteristics and volume capacity of the superabsorbent fibrous layer and the three-part laminated sheet (as noted by the disclosure within copending application of Messers. D'Elia and Hogan) are determined by many factors including superabsorbent fiber content, the composition of the support fiber material, batt density, and padding size. It is recognized also that the horizontal and vertical water retention properties of the absorbent fibrous layer will vary markedly with alterations in the nature and percentage content of superabsorbent fiber versus support fiber, the denier, the fabric weight, and the composition of the suppert fiber. If and when the preferred blend of heterocyclic carbonate and copolymer of maleic anhydride and isobutylene is employed, polyester is the most desirable material for use as the support fiber for combination with the superabsorbent fiber. Polyester contributes excellent absorbency properties adjunct and complementary to those of the absorption fibers themselves when present in sufficient density. Moreover, whenever finer denier of support polyester fibers is employed, the overall fluid retention capacity is clearly increased such that various embodiments of the preferred materials are able to absorb 60 fold and sometimes up to 100 fold their product weight of water or other fluid.

To illustrate and to understand how the laminated preferred construction for the superabsorbent fibrous lining works, FIG. 10 illustrates a cross-sectional view of the laminate construct in greater detail. The support fibers 80 are shown as solid lines while the superabsorbent fibers 78 are provided as dashed lines so that they can be distinguished from one another. The fluid-permeable covering stratum 72 permits the migration of fluids such as water and is typically hydrophobic to facilitate complete and rapid migration and transfer of fluid to the absorbent batt beneath it. An added and desirable function of the covering stratum 72 is to provide a smooth sliding surface of low surface tension which presents a relatively small coefficient of friction upon which the skin of the corpse or other object may be readily moved without tearing the absorbent batt material whether in dry or saturated form.

In the unused, dry state, both the superabsorption fibers and the support fibers may criss-cross and bend as indicated within FIG. 10. When the absorbent batt absorbs fluid and becomes wet, the superabsorbent fibers 78 can swell to many times their original dry size, up to and including about 100 times their diameter when dry. In addition, the swelling of the superabsorbent fibers upon wetting exerts force upon the support fibers 80 in the batt and stiffens them. Accordingly, in many instances, the absorbent batt forces fibers which are only loosely crossed and meshed in the dry state to tightly lock and support each other in the wetted fluid absorbent state. This mechanism is believed to account in part at least for the superabsorption capability of the fibrous layer to retain its physical integrity even when holding many times its weight in fluid.

It should be noted and appreciated also that a wide range and diversity of other compounds and chemical compositions are believed to be conventionally available and known as substitutes and replacements for the preferred composition for superabsorbent fibers as described above. The range, variety, and diversity of such superabsorbent materials and compositions is described within the following publications: water absorbing acrylic copolymer compositions prepared from acrylic acid monomers and hydrophilic unnsaturated carbonate monomers as described within Japanese Patent Publication No. 63242344 (881017); the water absorptive composites of impregnated natural or synthetic fibers with modified acrylic acid described within European Patent Publication No. 290814 (881117); water-swellable cross-linked polymers of vinyl-accharide monomer as described by European Patent Publication No. 283090 (880921); a superabsorbent for blood and proteinaceous fluid comprising insoluble ionic macromolecular material in acidic form as described within French Patent No. 2602985 (880226); water absorptive fibrous composite materials containing polymerized partially neutralized acrylic acid which is cross-linked using glycidyl ether compounds as described by European Patent Publication No. 232121 (870812); water-absorbing polymer compounds prepared by polymerization of acrylic acid (alkali metal) salts in the presence of alpha-olefins and carboxylic acids as described within Japanese Patent Publication No. 62053310 (870309); and a fluid absorbing composition comprising water soluble carboxylic polyelectrolyte cross-linked with di— or poly-functional aziridine as described within U.S. Pat. No. 4,645,789. It will be recognized and appreciated that the provided listing is merely illustrative and clearly nonexhaustive in its coverage. Many other fluid absorbing materials able to be manufactured and to provide a superabsorbent capability—that is, able to absorb at least 15 times its own weight in fluid—are clearly available and commercially sold today. All such conventionally known chemical compositions, manufacturers, and superabsorbent materials are deemed to be within the scope of the present invention.

The Internal Spacing Zone

An optional, but highly desirable and preferred, feature of the present invention is the construction and presence of an internal spacing zone between the outer shell and the superabsorbent fibrous lining. The presence of the internal spacing zone provides at least three benefits to the construction. Initially, the spacing zone acts as a protective buffer zone maintaining at least a layer of air between the outer shell and the superabsorbent fibrous lining; thus when the corpse or other object is placed inside the carrying container, the object is at least partially supported and protected from external impact by the layer of air within the spacing zone. Second, the internal spacing zone provides an open passageway or corridor not only for the placement of conduit tubing for the carrying of a freezible liquid and the gas channeling system for the piping of a refrigerant gas; but also serves as an open air pathway for the general flow of liquids and gases to and from the superabsorbent fibrous lining. Third, the internal spacing zone provides an area for placement of other optional but highly desirable features. Thus, the internal spacing zone provides an area for optional placement of a sheet of insulating material to be applied to the internal surface of the outer shell and which would enhance the pressure resistance of the carrying container as a whole. This spacing zone also would provide an area for the positioning of a pressure regulation safety valve such that if the refrigerant gas were introduced into the internal volume at too rapid a rate or at too great a cumulative pressure, the safety valve would release thereby preventing the rupture of the carrying container as a whole. This spacing zone would also serve for the placement of various germicidal and disinfecting agents as well as for chemical neutralization compositions which would provide both germicidal and chemical neutralization means to counteract such infectious or chemically dangerous fluids as are released by the object held within the internal volume of the carrying container.

Within the first preferred embodiment, the internal spacing zone is constructed via the use of flexible spacing fingers joined at their proximal ends to the internal surface of the outer shell while the distal ends of the spacing fingers remain free and mobile. The spacing fingers themselves are preferably constructed of an elastic material which provide both flexibility and elasticity; and thereby allows the internal spacing zone consequently created to be irregular both in dimensions and volume. The use of such spacing fingers, however, is purely an optional feature, as is the construction of the internal spacing zone itself. Any means of creating an internal spacing zone, any construction mode, and any design parameter may be employed in place of the spacing fingers described in the first preferred embodiment. Any and all of these alternatives are deemed to be within the scope of the present invention.

The Freezible Liquid Conduit System

It is clear from FIGS. 2-7 inclusive that the conduit system described therein is merely one form and one construction of the on-demand means in communication with the internal volume of the enclosed carrying container for the introduction of a freezible liquid to the superabsorbent fibrous lining. The conduit system as described includes the major and minor tubes, the connecting hoses, and the reservoirs initially holding a freezible liquid. This system constitutes one preferred means to achieve the intended result on-demand. The tubing of the conduit system preferrably is prepared from a resilient, fluidimpermeable material which can retain its shape as a conduit and which will not react chemically or otherwise with the freezible liquid being transported by the system. Clearly, the diameter, degree of branching, and rate at which the freezible liquid is conveyed may vary greatly among different embodiments and subsequently is of no major import or consequence. Similarly, the manner in which the internal conduit system is connected to a source of freezible liquid positioned outside the shell of the carrying container; and the manner in which the freezible liquid is held until required or desired to be introduced to the superabsorbent fibrous lining; is a matter of personal choice and convenience.

The Freezible Liquid

The user also has a wide variety of different freezible liquids among which to choose for use with the present invention. Most desirable is the use of water without any additives whatsoever. Water, regardless of whether pure or impure, can be found almost anywhere under almost every kind of conceivable condition and circumstances. While the first preferred embodiment desirably provides for reservoirs of a freezible liquid such as water to be transported by the rescue team to the intended site of use, this is clearly not a requirement of the present invention. To the contrary, because water is almost universally available, it is intended and expected that a source of water will be present at the site of finding the corpse (or the place of obtaining the object to be transported) in sufficient quantity as to be able to be introduced on-demand to the superabsorbent fibrous lining. Thus, water is the most preferred freezible liquid for use with the present invention.

In the alternative, a wide variety of other freezible liquids are available to the user, the majority of which are aqueous based. Such freezible liquids are represented by the descriptions of U.S. Pat. Nos. 4,745,909 and 4,742,958 among others. The text of these U.S. Patents are therefore expressly incorporated by reference herein. Thus, a fluid gel which is made from starch and water and usually prepared with a preservative or bacteriocide to prevent organic action is an alternative composition acceptable for use. Similarly, the water swellable materials conventionally known including all polymers, copolymers, and terpolymers capable of swelling in an aqueous solution are also within the scope of the present invention. It will be recognized and appreciated, however, that any liquid capable of being introduced to the superabsorbent fibrous lining of the closed container which will then freeze upon exposure to a refrigerant gas is within the scope of the present invention.

The Refrigerant Gas Channeling System

Clearly, the refrigerant gas channeling system described as a constituent part of the first preferred embodiment is merely one preferred construction of the requisite on-demand means in communication with the internal volume of the closed container for the introduction of a refrigerant gas to the superabsorbent fibrous lining. Within the first preferred embodiment, the gas channeling system comprises a system of gas piping of major and minor pipes in flow communication with a gas main, and a gas regulation valve. This mode of construction allows the introduction of a refrigerant gas from an external source to be channeled from the exterior of the carrying container into intimate contact with the superabsorbent fibrous lining within the internal volume of the container. As noted within FIGS. 2-7, the system of gas piping is desirably positioned within the internal spatial zone separating the outer shell and the superabsorbent fibrous lining. This is a highly desirable and preferred positioning because it removes the system of gas piping from direct contact with the corpse or other objects held and surrounded by the superabsorbent fibrous lining; and thus diminishes the risk of injury or alteration to the corpse or object as a consequence. In the alternative, however, should the user desire or require, the system of gas piping may be positioned within the internal volume provided by the interior surface of the superabsorbent fibrous lining and thus lie adjacent to and be in intimate contact with the corpse or object being carried. While this alternative placement is less preferable, this mode of construction nevertheless provides ondemand means for introducing a refrigerated gas to the superabsorbent fibrous lining when and as desired by the user.

As will be described hereinafter in the second and third preferred embodiments, the internal placement of a channelled system of gas piping (whether within the internal spacing zone or within the confines and interior volume provided by the fibrous lining itself) is an optional construction and design; accordingly, the entire system of gas piping positioned within the internal volume of the closed container regardless of precise location or placement may be eliminated entirely. As will be recognized from the descriptions of the second and third preferred embodiments hereinafter, it is the internal spacing zone itself which then serves as a passageway and corridor for the flow of the refrigerant gas throughout the entirety of the closed container and causes the freezing of all liquids that have been absorbed by the superabsorbent fibrous lining.

Figure 11C:
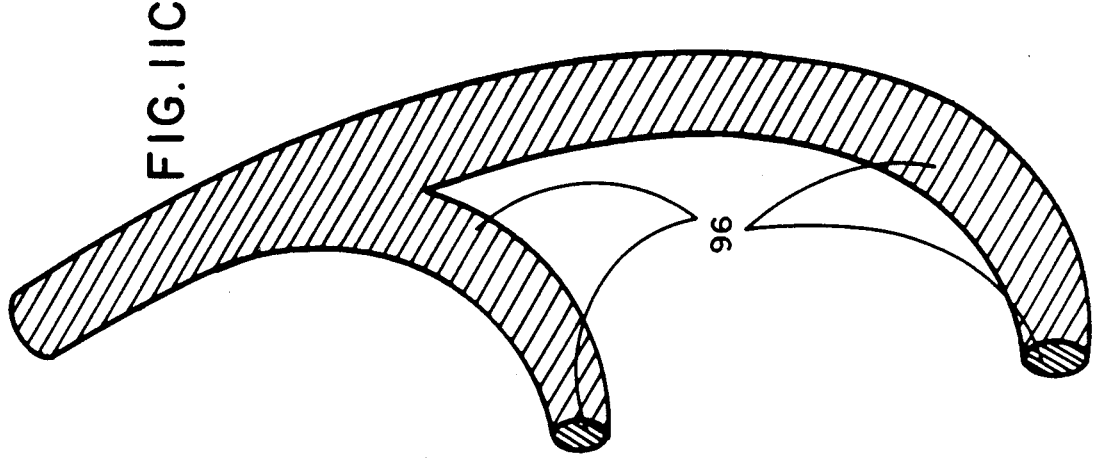
FIGS. 11a–11c are alternative illustrations of channel pipes useful for introducing a refrigerant gas to the superabsorbent fibrous lining of the embodiment illustrated by FIG. 2.
Figure 11B:
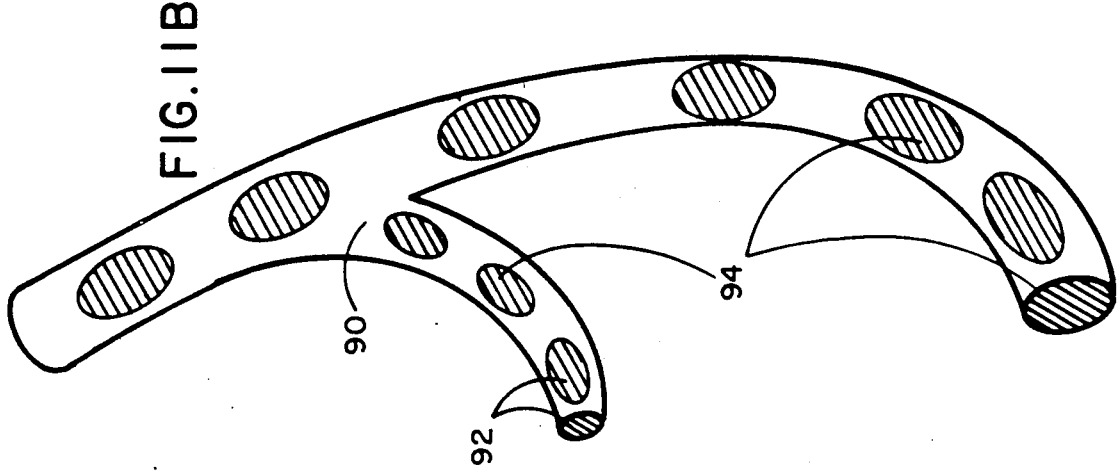
Figure 11A:
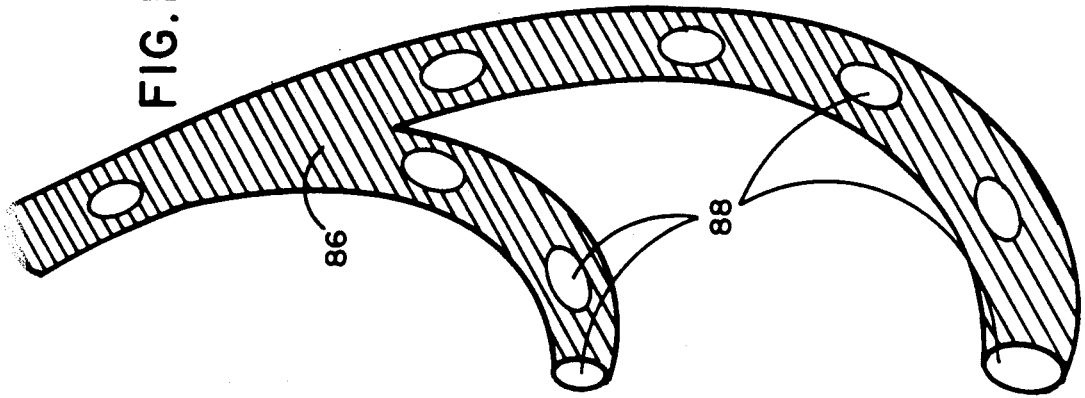

Nevertheless, in the first preferred embodiment, the system of gas piping constituting major and minor pipes can take a variety of different forms in and of itself as illustrated by FIGS. 11a-11c respectively. As appears in FIG. 11a, the pipes are constructed as a series of branched ducts 86 having a plurality of apertures 88 along its length and ends. The placement of the apertures 88 is a personal choice which allows the user to provide a smaller or greater range of gas density, pressure, and rate of gas transfer for the system. An alternative mode of construction is illustrated by FIG. 11b which shows a branched pipe 90 having a plurality of apertures 92, all of which are covered by a gas-permeable but liquidimpermeable membrane. By this construction, such freezible liquid as may accidentally come into contact with the gas channeling system will be prevented from entering the system of gas piping itself by the membranes 94 covering each aperture 92. In this manner, such liquid as would otherwise freeze and block the aperture is thus minimized in effect by this particular construction. A third construction alternative is illustrated by FIG. 11c which shows a gas channel 96 constructed entirely of gas-permeable but fluid-impermeable material. In this construction, the entirety of the gas channel 96 acts over all its surface area and volume to release the refrigerant gas; and any particular zone of the gas channel which may accidentally come in contact with the freezible liquid is not sufficient to block or obscure the flow of the refrigerant gas through the remainder of the channel.

The Refrigerant Gas

A wide variety of conventionally known refrigerant gases are available for use in the present invention. Most desirable are those gases which are environmentally compatible and form constituent parts of the ambient air. Accordingly, compressed carbon dioxide, oxygen, or nitrogen are desirably employed as the refrigerant gases of choice. In addition, other known refrigerant gases which provide temperatures in the range of about $-40°$ to $31°$ F. at a minimal pressure (preferably less than 20 pounds per square inch) are also deemed to be useful. These include: dichloro-difluoro-methane (Refrigerant 12); monochlorodifluoro-methane (Refrigerant 22); and dichloro-tetrafluoroethane (Refrigerant 114). It is also expected that a variety of different inert gases such as compressed helium, argon, and the like may also be employed as alternatives.

Depending upon the refrigerant gas employed, it is believed that the freezible liquids absorbed by the superabsorbent fibrous lining (or alternatively the freezible solid coating applied to the superabsorbent fibrous lining) will become frozen immediately upon contact with the refrigerant gas introduced into the internal volume of the closed container. Since the refrigerant gas is expected to provide a contact temperature ranging from less than $32°$ F. to about $-40°$ F., the frozen liquid (or frozen solid coating) generated by the refrigerant gas will then provide refrigeration for the contents of the carrying container for a time period ranging between about 4-8 hours. The time duration for the cooling will vary with the size of the carrying container, the quantity of freezible liquid (or solid coating present on or) within the superabsorbent fibrous lining, the temperature and moisture of the geographical area where the carrying container is employed, and the heat generated or released by the corpse or object being housed within the carrying container itself. An optional, but useful, addition to the minimal construction requirements of the present invention is the inclusion of a small thermometer or other temperature measuring gauge which extends into the internal volume of the carrying container but provides a display which is positioned externally on the outer shell of the container. By this simple addition, the internal temperature and cooling effect can be monitored at a glance; and the rate at which the frozen liquid (or solid coating) reverts to a non-frozen state can be effectively followed.

It is expected also that there will be instances in which it will take substantially longer than 8 hours to remove and transport the corpse or other object held within the carrying container from the initial site of discovery to a desired receiving location. The refrigeration capacity provided by the present invention will diminish over time with a complete reversion to the non-refrigerated state within approximately 8 hours duration. The present invention intends, however, that periodic and repeated introductions of the refrigerant gas will be made on a regular or irregular basis on these occasions. Accordingly, as the cooling capacity decreases over time, the user—at will and at a time and place of his own choosing—can introduce a second, and a third, and a fourth charge, as well as additional charges of refrigerant gas to the freezible liquid (or solid coating) held by the superabsorbent fibrous lining. Each repeated charge of refrigerant gas will cause such unfrozen liquid (or solid coating) to refreeze completely immediately upon contact with the refrigerant gas. In this manner, the cooling capacity of the carrying container is periodically recharged completely to its maximum extent again and again until the desired destination point is reached.

A Second Preferred Embodiment

Figure 12:
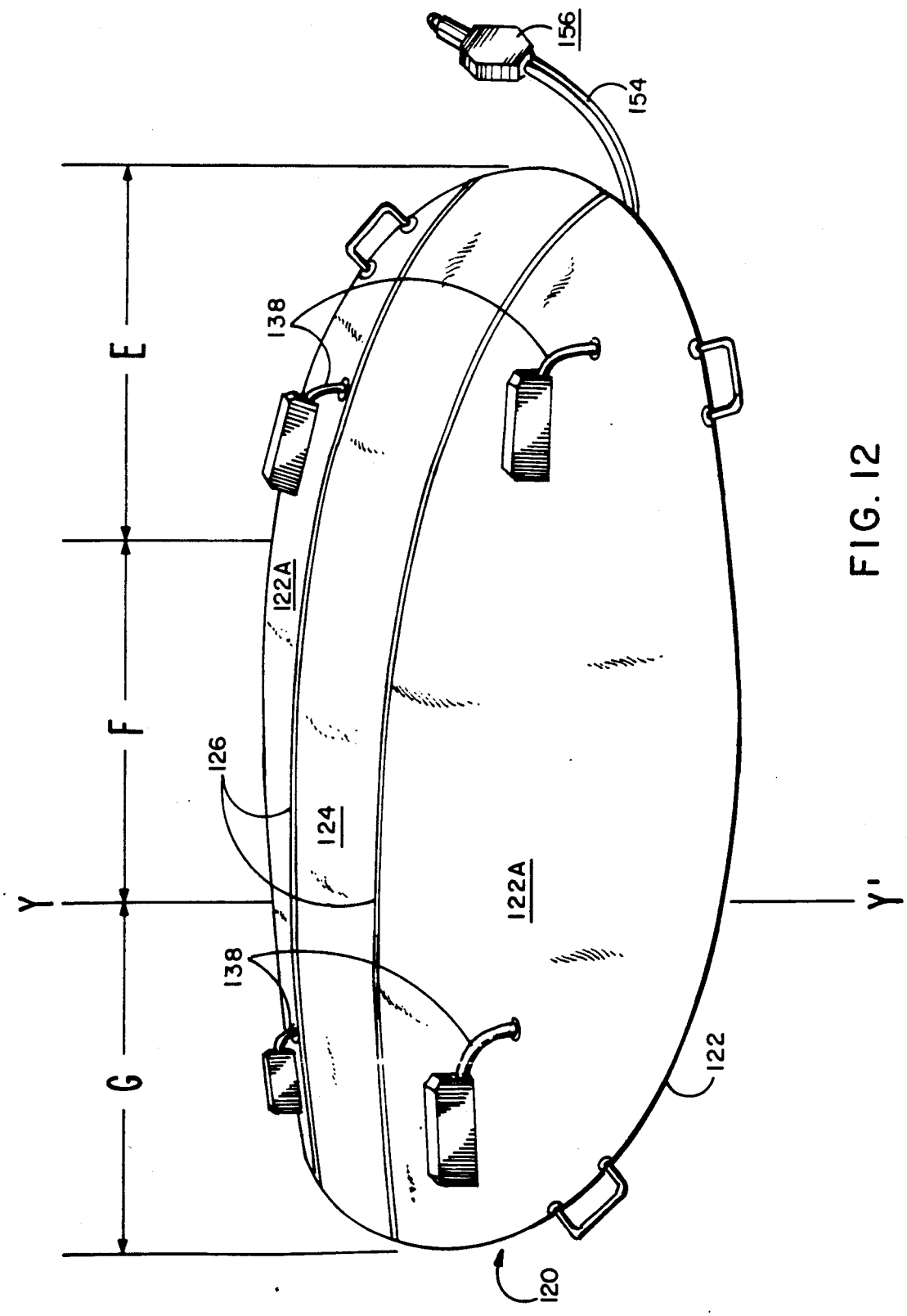
FIG. 12 is a perspective view of a second preferred embodiment of the carrying container which comprises the present invention.
Figure 13:
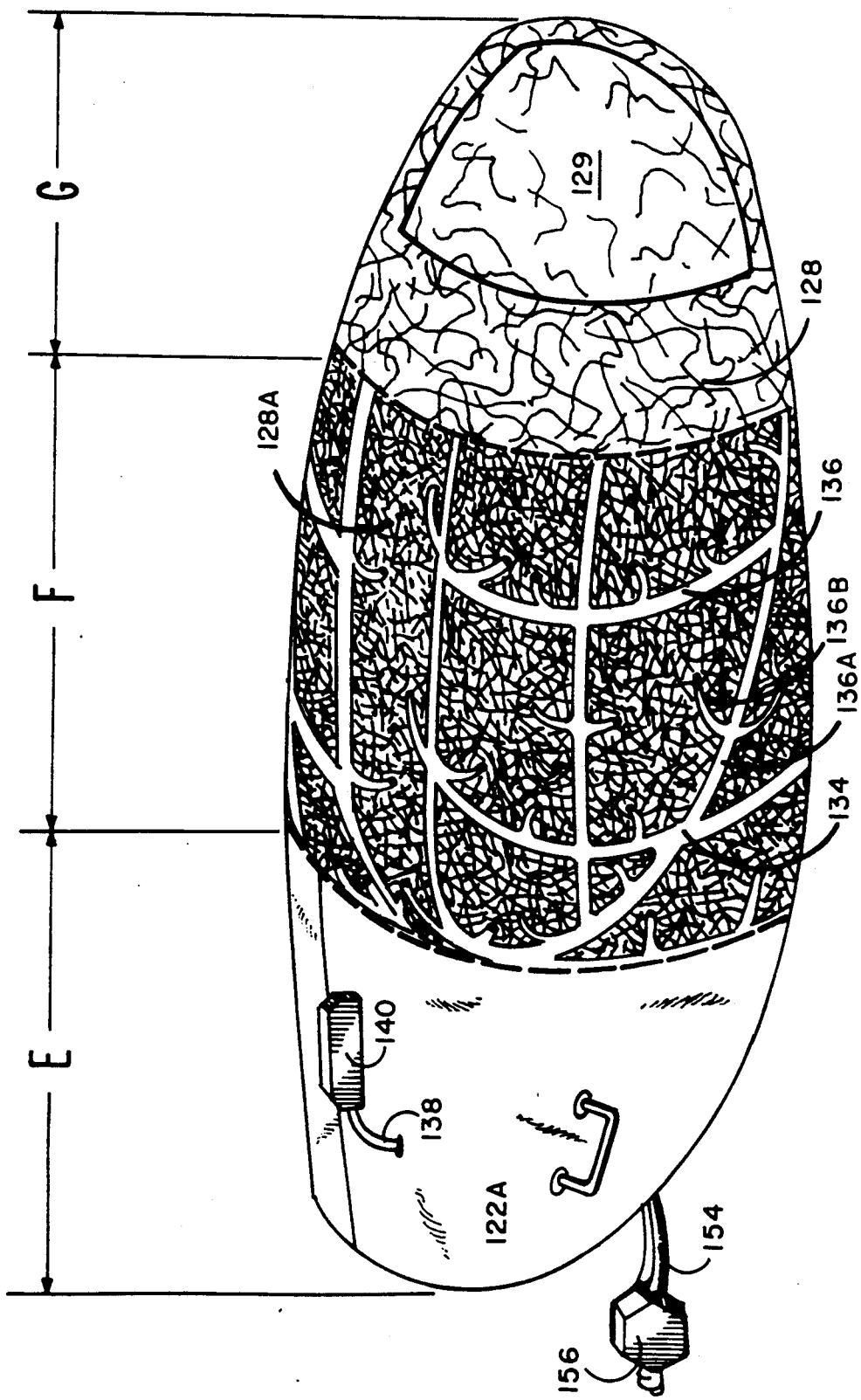
FIG. 13 is a perspective break-away view of the different components comprising the carrying container illustrated by FIG. 12.
Figure 14:
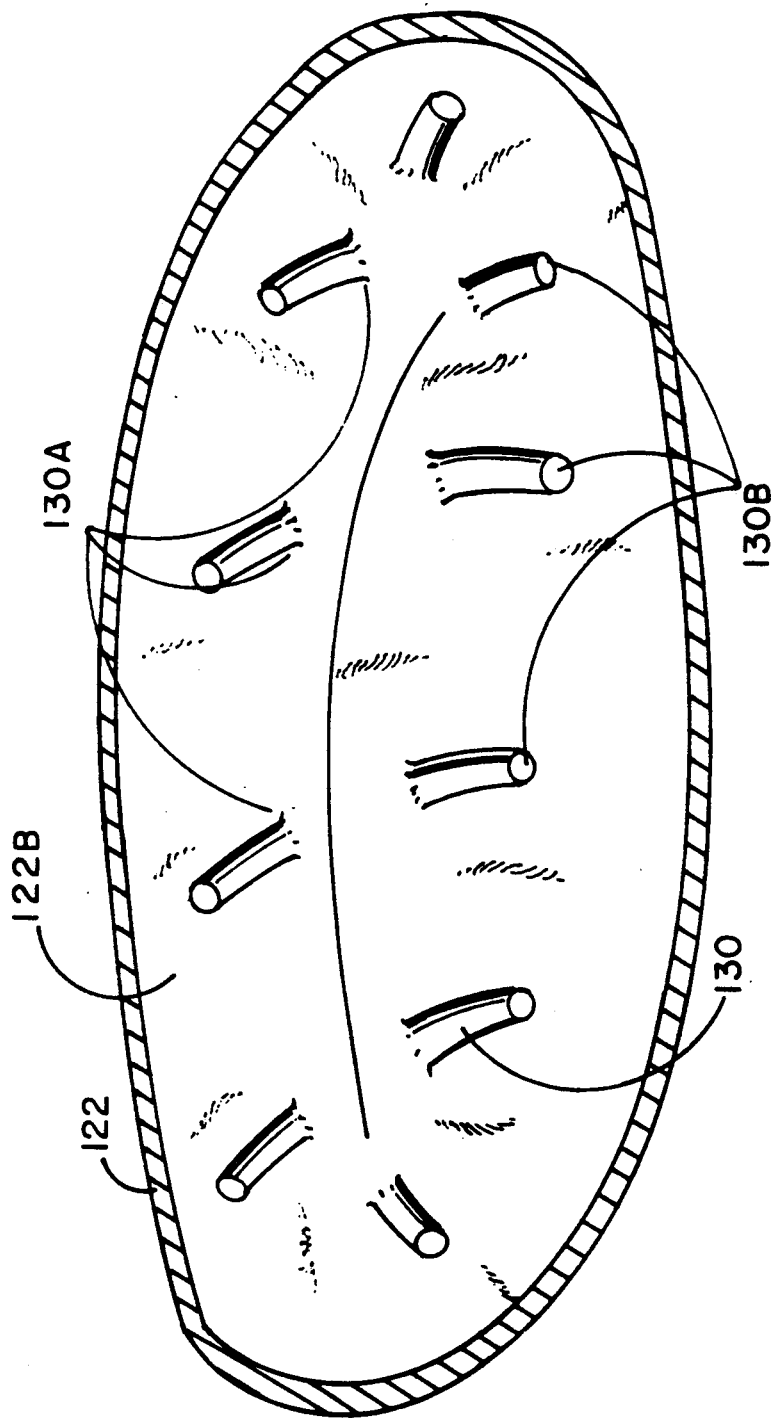
FIG. 14 is an underside view of the outer shell of the carrying container illustrated by FIG. 12.
Figure 15:
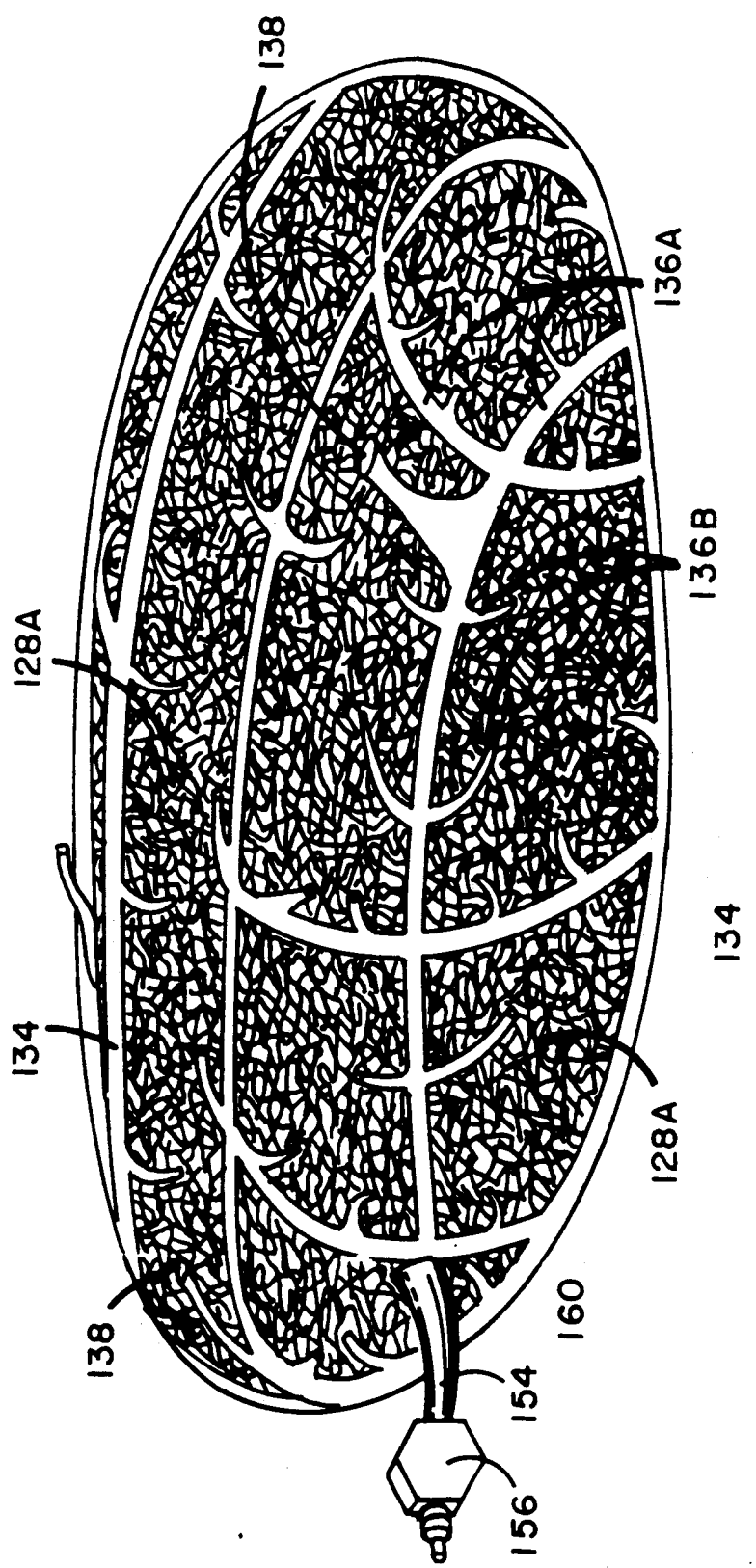
FIG. 15 is a perspective view of the carrying container of FIG. 12 after the outer shell has been removed.
Figure 16:
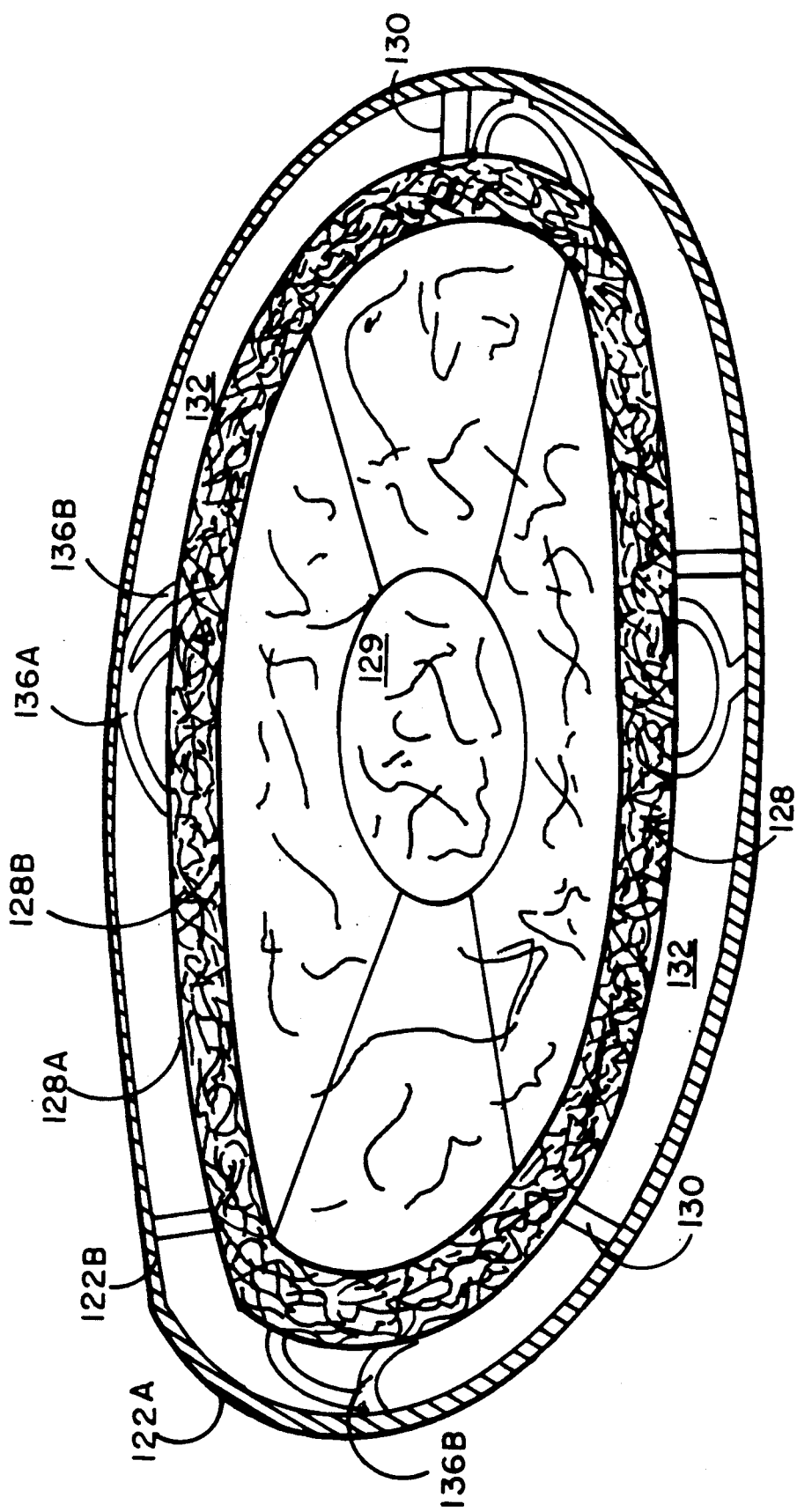
FIG. 16 is a cross-sectional view of the embodiment illustrated by FIG. 12 along the axis yy'.

A second preferred embodiment is illustrated by FIGS. 12-16 respectively. As seen therein, FIGS. 12 and 13 provide overhead perspective views and breakaway perspective views of this second embodiment. In comparison, FIGS. 14 and 15 illustrate the individual layers of the construction while FIG. 16 is a cross-sectional view along the axis yy' of the embodiment shown within FIG. 12.

As shown by FIGS. 12-16 inclusive, a carrying container 120 is shown which is divided into individual zones E, F, and G for clarity, with H indicating the internal spatial volume of the container. The carrying container comprises an outer shell 122 and includes a closure flap 124 and a fluid-tight closure 126. The outer shell 122 comprises one wall and has a determinable internal volume and spatial configuration. The closure flap 124 and the fluid-tight closure 126 provide the means for inserting and removing an object from the spatial volume provided within the closed container 120.

While the outer surface 122a of the outer shell 122 appears as shown in FIG. 12, the inner surface 122b of the outer shell appears as shown in FIG. 14. A plurality of flexible spacing fingers 130 are joined at their proximal ends 130a to the inner surface 122b while the distal ends 130b extend inwardly and abutt the external surface 128a of the superabsorbent fibrous lining 128. The abuttment of the spacing fingers 130 against the superabsorbent fibrous lining 128 creates an internal spacing zone 132 as is shown by FIG. 16. The internal spacing zone 132 provides an open passageway or corridor in this second preferred embodiment for the positioning of the freezible liquid conduit system 134 and the refrigerant gas channeling system 150.

The freezible liquid conduit system 134 is shown most clearly by FIGS. 13, 15, and 16 respectively. As shown therein, the system includes the positioning on the outer surface 122a of the outer shell of four reservoirs 140; which are individually joined to connecting hoses 138; which in turn extend into the interior spatial volume of the carrying container 120. Each of the connecting hoses 138 are in flow communication with the internal major tubes 136a and minor tubes 136b which are positioned within the volume provided by the internal spacing zone 132 and extend over the entire length coextensive with the superabsorbent fibrous lining 128. The open ends of the minor tubes 136b abut and lie adjacent to the external surface 128a of the superabsorbent fibrous lining 128 as shown. A freezible liquid 142 held within the reservoirs 140 is released on-demand by the user. Once released, the freezible liquid 142 flows through the connecting hoses 138 into the major tubes 136a and the minor tubes 136b to the external surface 128a of the superabsorbent fibrous lining 128 where the freezible liquid is absorbed in its entirety.

The refrigerant gas channeling system 150 appears most clearly within FIGS. 12, 15, and 16 inclusive. As shown therein, a gas main 154 and a gas regulation valve 156 appears external to the carrying container 120 and extends through the outer shell 122 into the internal spacing zone 132. The gas main 154 terminates abruptly at the internalized end 160 and is secured in position using conventional means. Unlike the first preferred embodiment described earlier herein, there is no system of gas piping and there are no major or minor pipes whatsoever at any position within the internal volume provided by the outer shell 122. Instead, when a refrigerant gas 158 is introduced through the gas regulation valve 156 and flows through the gas main 154 into the internal volume of the carrying container, the refrigerant gas is released freely from the internalized end of the gas main 160 directly into the internal spacing zone 132. Once released, the refrigerant gas flows through the open passageways and corridors provided by the internal spacing zone 132 coming into direct and intimate contact with the entirety of the external surface 128a of the superabsorbent fibrous lining 128. It is therefore the internal spacing zone 132 which acts as the effective pathway and channeling system for the distribution of the refrigerant gas within the internal volume of the carrying container.

Once the refrigerant gas has been released into the internal spacing zone 132, the gas flows freely under pressure and will cause the freezing of all liquids previously absorbed by the superabsorbent fibrous lining 128. In this manner, both the previously introduced freezible liquid 142 and such fluids as may have been released by the corpse or other object held within the container become frozen immediately after contact with the refrigerant gas. It will be recognized and appreciated that the porous nature of the superabsorbent fibrous lining allows the refrigerant gas to pass through the entire thickness and length of the superabsorbent fibrous lining 128 and to pass into the central cavity 129 where the corpse or other object is contained. Once frozen, a coolant capacity of from 4-8 hours duration is provided.

A THIRD PREFERRED EMBODIMENT

A third preferred embodiment is illustrated by FIGS. 17-21 respectively. Perspective overhead views and break-away perspective views of the embodiment are provided by FIGS. 17 and 18 individually in which individual zones are indicated by J, K, and L, with M representing the internal cavity space of the carrying container. Individual views of the outer shell and internal construction of this third embodiment are provided by FIGS. 19 and 20 while a cross-sectional view of this embodiment along the axis xx' is provided by FIG. 21.

Figure 17:
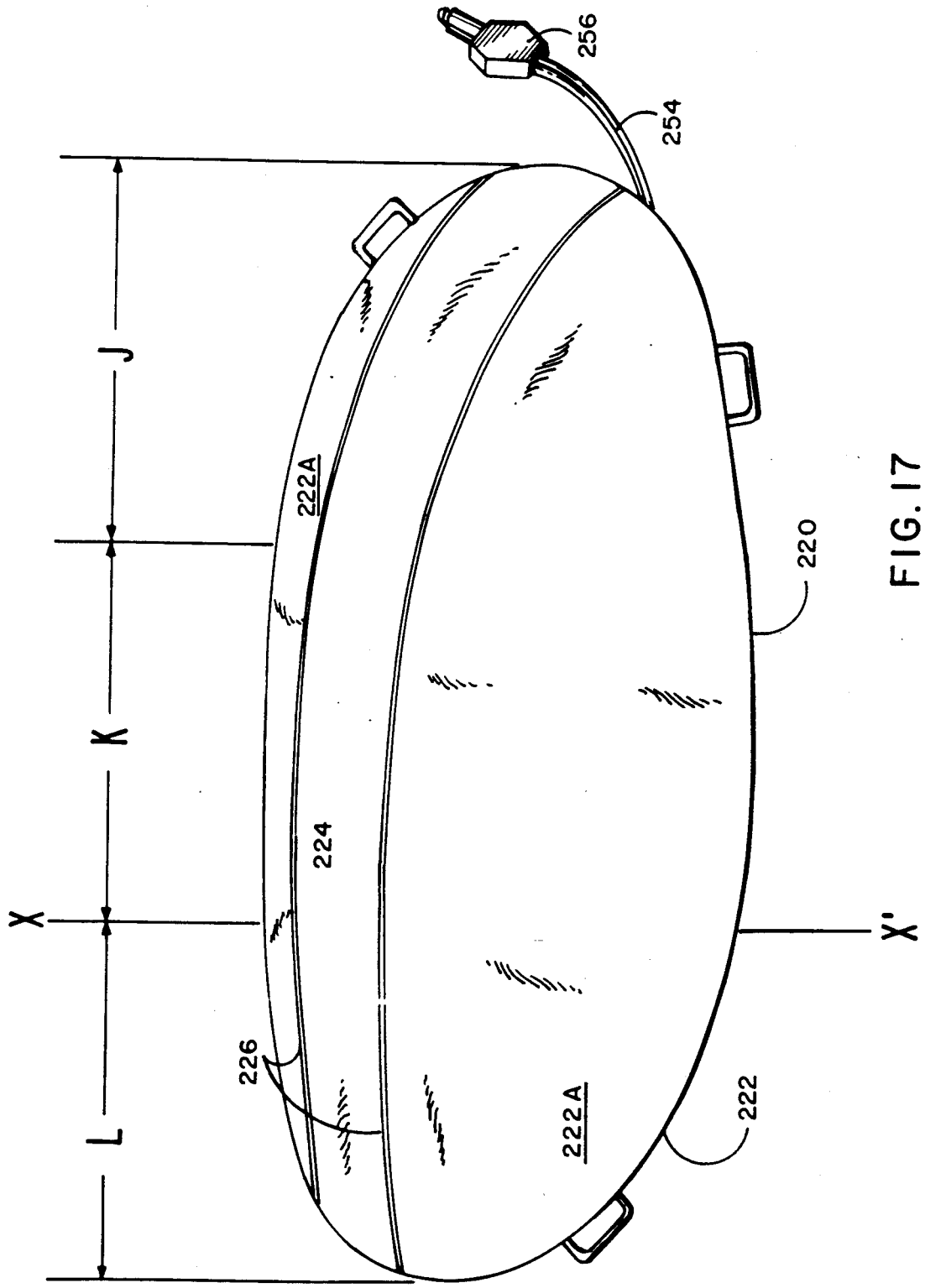
FIG. 17 is a perspective view of a third preferred embodiment of the carrying container comprising the present invention.
Figure 18:
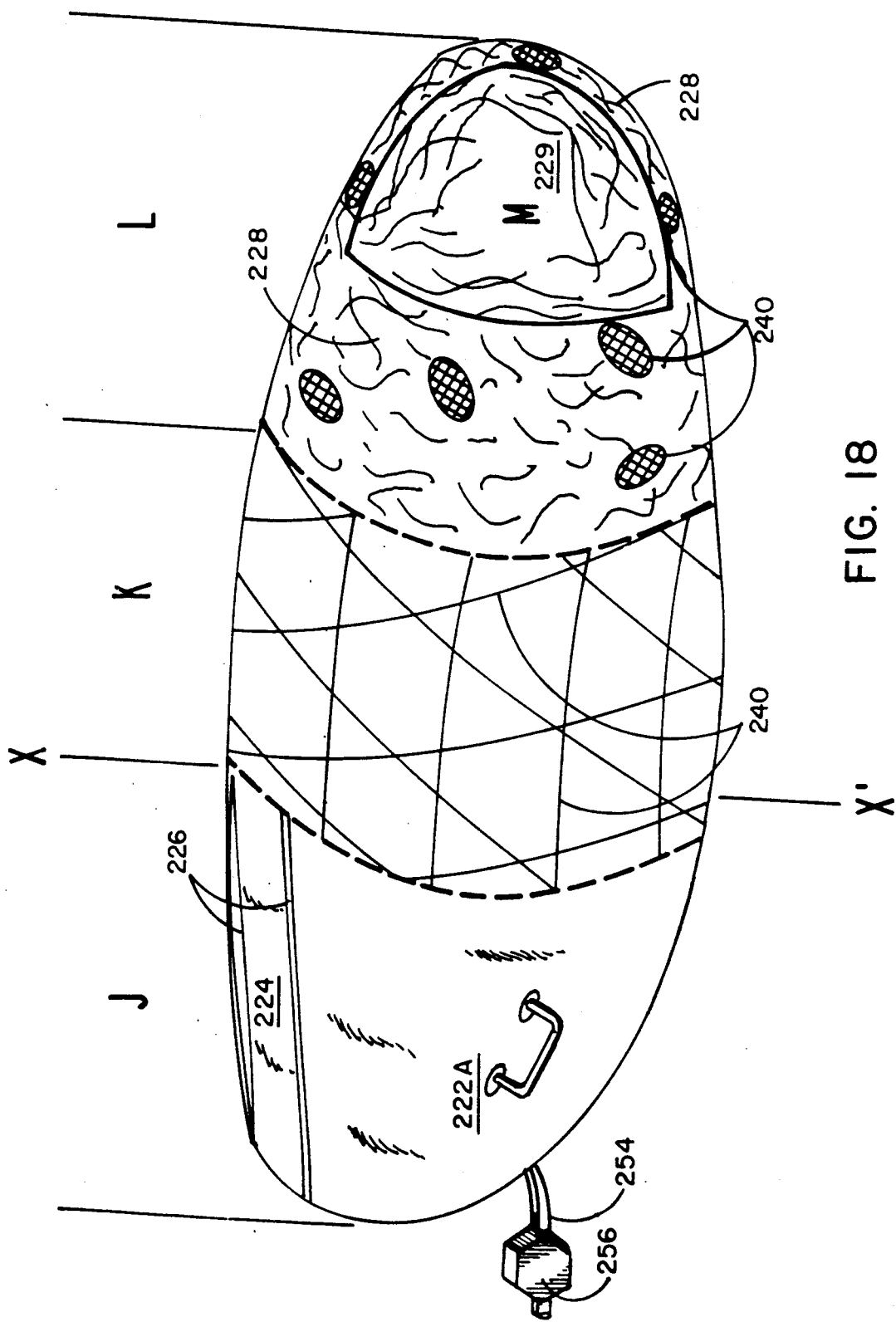
FIG. 18 is a break-away perspective view of the embodiment illustrated within FIG. 17 showing the various components of the carrying container.
Figure 19:
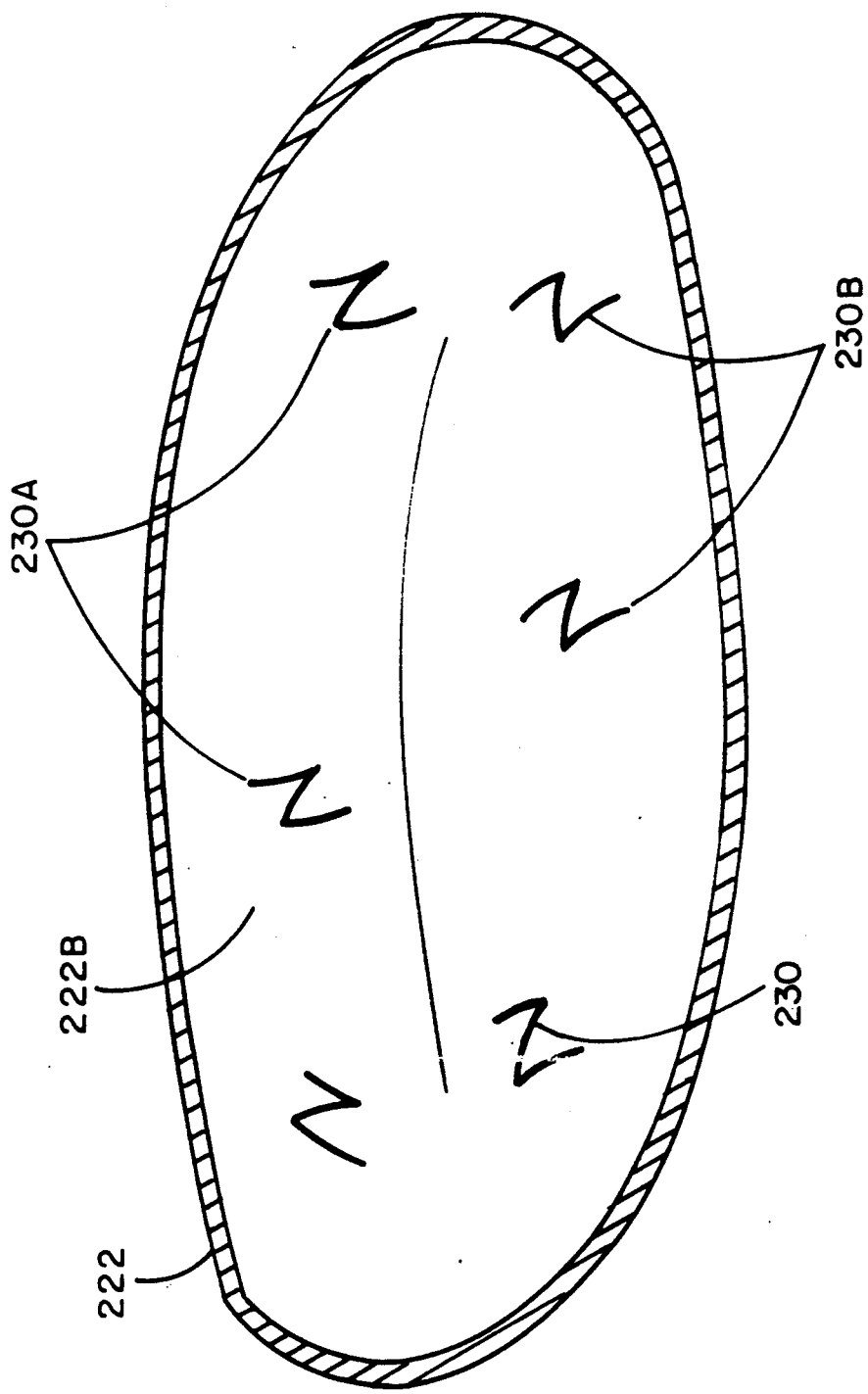
FIG. 19 is a view of the underside of the outer shell layer of the embodiment illustrated by FIG. 17.

As appears in FIGS. 17 and 18, a carrying container 220 is shown comprising an outer shell 222, a closure flap 224, and a fluid-tight closure 226. The outer shell 222 is preferably composed of a fluid-impermeable material and the combination of the closure flap 224 and the closure 226 provide the means for inserting and removing an object from the spatial volume provided by the outer shell 222. While the outer surface 222a of the outer shell 222 is unremarkable, the inner surface 222b shown by FIG. 19 has a plurality of flexible "Z-shaped" spacing joints 230 extending inwardly. The proximal ends 230a of each spacing joint 230 are permanently joined to the inner surface 222b of the outer shell while the distal ends 230 of the spacing joints extend radially towards and abutt the superabsorbent fibrous lining 228. In this manner, an internal spacing zone 232 is created bounded by the external surface 228a of the superabsorbent fibrous lining 228 and the inner surface 222b of the outer shell 222.

Figure 20:
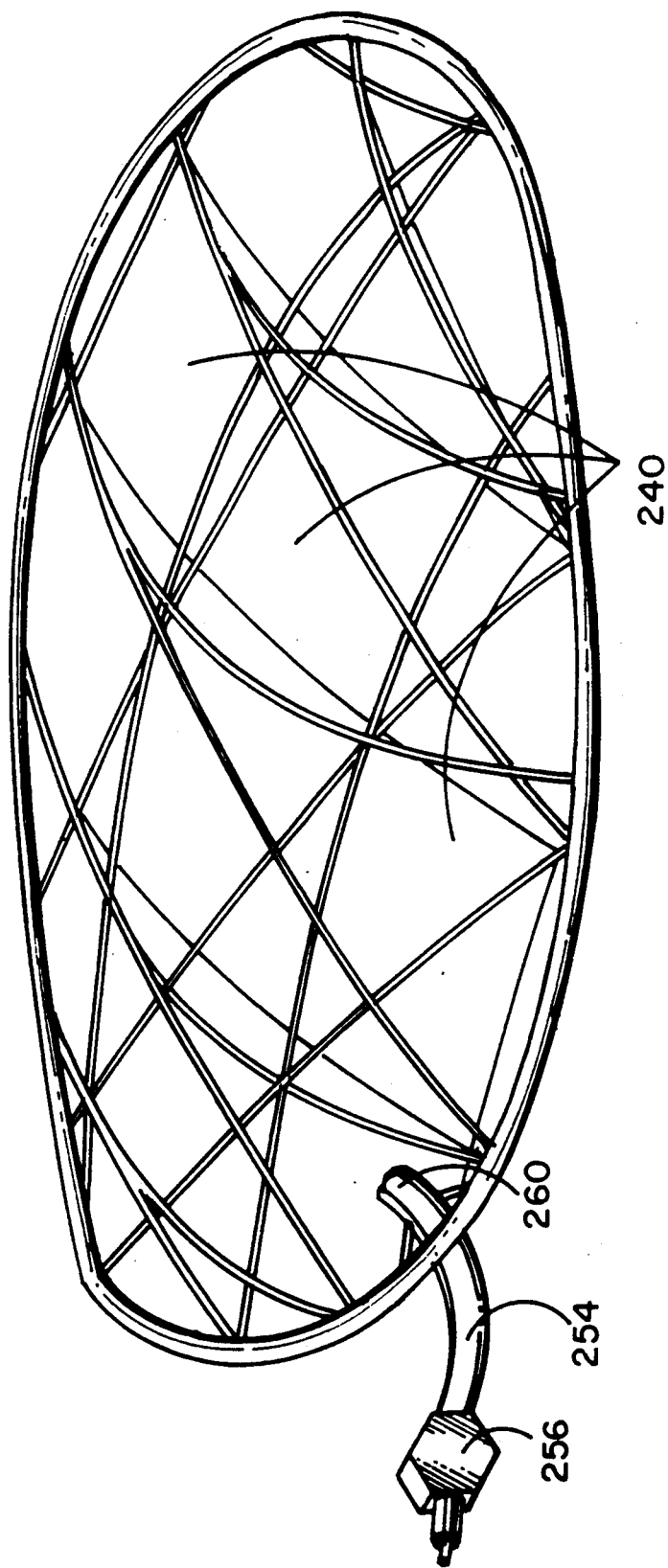
FIG. 20 is a perspective view of the embodiment illustrated by FIG. 17 after the outer shell has been removed.
Figure 21:
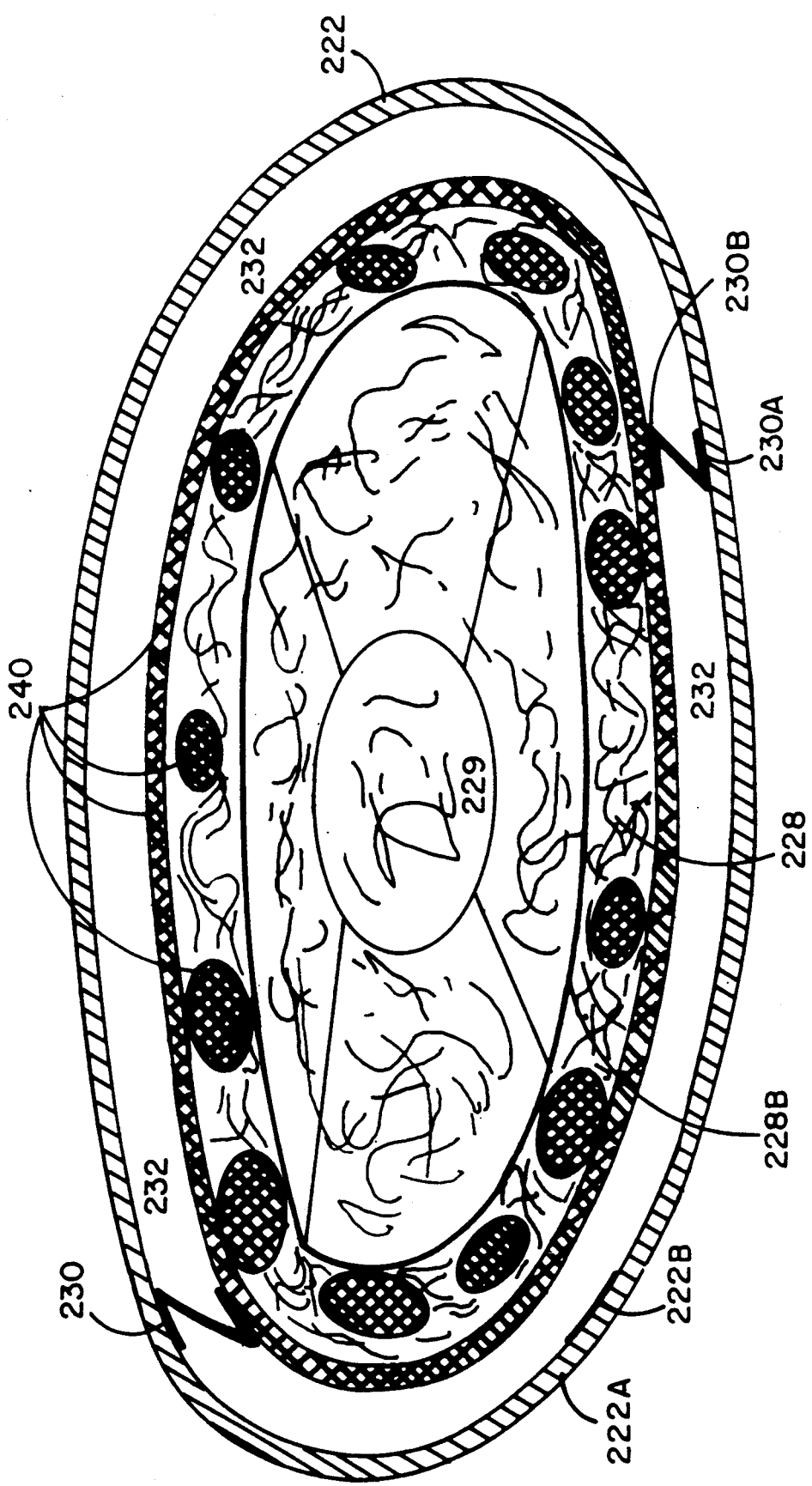
FIG. 21 is a cross-sectional view of the embodiment illustrated by FIG. 17 along the axis xx'.

In this embodiment, as illustrated by FIGS. 18, 20, and 21 inclusive, the superabsorbent fibrous lining 228 is coated over its external surface 228a with a freezible solid coating material. While this solid coating 240 appears to cover the entirety of the external surface 228a in this third embodiment, it is required only that the freezible coating 240 be applied to only at least a portion of the superabsorbent fibrous lining 228. In addition, as is shown by FIG. 21, it is expected that the material comprising the freezible solid coating 240 will penetrate into the thickness of the superabsorbent fibrous lining 228 in a meaningful degree. Although the degree of penetration is expected to be variable, the internal penetration provides a greater quantity of freezible solid ready to be frozen on-demand.

The composition of the freezible solid coating applied to the superabsorbent fibrous lining is expected to be one chosen from among the conventionally known formulations commercially sold or reported in the scientific literature. A preferred freezible solid coating material is disclosed within U.S. Pat. No. 4,357,809, the text of which is expressly incorporated by reference herein. The solid coating material is desirably a solid gel which preferably is composed of about 15% by weight of corn starch, borax in the amount of about 2% by weight of the corn starch, about 0.01% by weight of a non-toxic preservative, and about 84.7% by weight of water. This solid gel material is said to never melt, not evaporate, and be self-sealing against punctures. Moreover, the solid gel material can undergo repeated freeze and thaw cycles without degrading or breakdown into a liquid state. In addition, it is expected that many other formulations, typically known as "hydrogels," can be prepared to meet specific needs or desires of the user as required.

The refrigerant gas channeling system 250 is best shown by FIGS. 17, 20, and 21 inclusive. As shown therein, the refrigerant gas channeling system 250 comprises a gas regulation valve 256 and a gas main 254 which appears external to the outer shell 222 of the carrying container 220 and extends through the outer shell into the internal spacing zone 232. The internalized end of the gas main 260 is secured within the passageway defined by the internal spacing zone 232 and releases an introduced refrigerant gas 258 into the volume of the internal spacing zone 232 on-demand. Once released, the refrigerant gas of choice 258 is distributed within and flows freely through the entirety of the internal spacing zone 232 thereby making direct intimate contact with the freezible solid coating 240 forming part of the pathway. The consequence of contact between the refrigerant gas and the freezible solid coating 240 disposed upon the superabsorbent fibrous lining 228 is the immediate freezing of the coating material into a solidified, frozen state. The entirety of the solid coating 240 both on the external surface 228a and that which has penetrated into the thickness of the superabsorbent fibrous lining 228 will become immediately frozen. In addition, any and all fluids or liquids released by the corpse or object contained within the central cavity 229 bounded by the internal surface 228b of the superabsorbent fibrous lining 228 will also become frozen as a concommitant consequence and result. Once frozen into a solid state, the solid coating 240 will provide refrigeration and efficient cooling capacity for up to 8 hours duration before a subsequent charge of a refrigerant gas need be introduced again.

OTHER ALTERNATIVE EMBODIMENTS

By the description of the three preferred embodiments disclosed herein, all of which are merely representative of the subject matter as a whole which is the present invention, it is expected and intended that a variety of other embodiments can and will be constructed. The preferred first, second, and third embodiments serve merely as desirable, illustrative examples of the mode of construction and the interrelationships among the requisite components parts which comprise the present invention. It is intended, however, that many modifications and variations of the constructions, materials, and designs disclosed herein can and will be made; all of these however are deemed to be within the scope of the present invention.

Figure 22B:
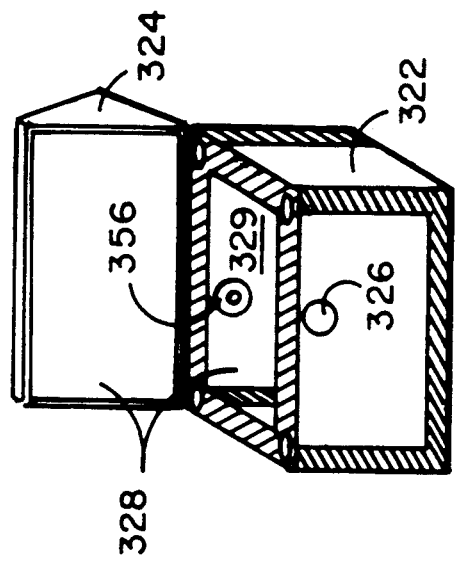
FIGS. 22a and 22b are alternative embodiments of the present invention designed for carrying food or beverages.
Figure 22A:
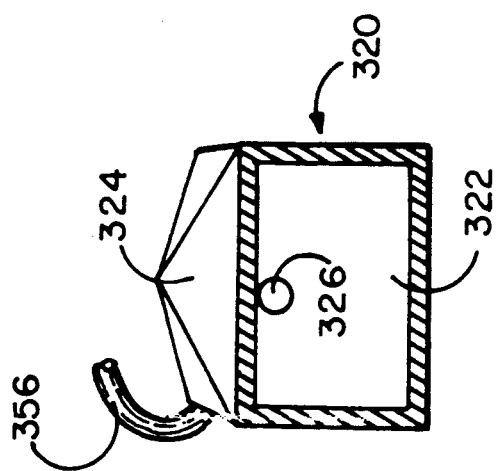

As merely one alternative format, the constructions illustrated by FIGS. 22a and 22b are provided. These are configured in the shape of the commonplace "picnic basket" or insulated cooler which is ordinarily brought by a person to the seashore, the mountains, or on vacation. The carrying container 320 is constructed with a rigid or flexible outer shell 322 and has a top flap 324 and closure 326. The interior of the carrying container 320 has a superabsorbent fibrous lining 328. In this construction, it is expected that the superabsorbent fibrous lining 328 rests and abutts the outer shell 322 with no intervening space whatsoever. The user merely adds water or any other freezible liquid directly to the superabsorbent fibrous lining 328; closes the top flap 324 using the closure 326; and then introduces a refrigerant gas 358 via the pipe 356 directly into the central cavity 329 where the food or beverage has been previously placed. The introduction of the refrigerant gas freezes the water or other freezible liquid purposefully introduced into the superabsorbent fibrous lining; and provides a frozen refrigerant and coolant capacity which will keep the food or beverage housed within the carrying container cold for up to 8 hours duration.

The present invention is not to be restricted in form nor limited in scope except by the claims appended hereto.

What I claim is:

1. A portable, superabsorbent carrying container able to provide refrigeration on-demand for its contents, said carrying container comprising:
    a portable, closed container comprising at least one wall and having a determinable internal volume and spatial configuration;
    at least one superabsorbent fibrous lining disposed within the internal volume of said closed container;
    means for inserting and removing an object from the spatial volume provided by said superabsorbent fibrous lining within said closed container;
    first on-demand means in communication with the internal volume of said closed container for introducing a freezible liquid to said superabsorbent fibrous lining on-demand, such freezible liquid as is introduced via said first on-demand means being absorbed by said superabsorbent fibrous lining; and
    second on-demand means in communication with the internal volume of said closed container for introducing a refrigerant gas to said superabsorbent fibrous lining on-demand, such refrigerant gas as is introduced via said second on-demand means causing the freezing of such liquids as have been absorbed by said superabsorbent fibrous lining.

2. A portable, superabsorbent carrying container providing refrigeration on-demand for its contents, said carrying container comprising:
    a portable, closed container comprising at least one wall and having a determinable internal volume and spatial configuration;
    at least one superabsorbent fibrous lining disposed within the internal volume of said closed container;
    means for inserting and removing an object from the spatial volume provided by said superabsorbent fibrous lining within said closed container;
    first on-demand means in communication with the internal volume of said closed container for introducing a freezible liquid to said superabsorbent fibrous lining on-demand, such freezible liquid as is introduced via said first on-demand means being absorbed by said superabsorbent fibrous lining;

second on-demand means in communication with the internal volume of said closed container for introducing a refrigerant gas to said superabsorbent fibrous lining on-demand, such refrigerant gas as is introduced via said second on-demand means causing the freezing of such liquids as have been absorbed by said superabsorbent fibrous lining;

a portable source of a freezible liquid in flow communication with said first on-demand means; and a portable source of a refrigerant gas in flow communication with said second on-demand means.

3. A portable, superabsorbent carrying container able to provide refrigeration on-demand for its contents, said carrying container comprising:

a portable, closed container comprising at least one wall and having a determinable internal volume and spatial configuration;

at least one superabsorbent fibrous lining disposed within the internal volume of said closed container, said superabsorbent fibrous lining being at least in part internally spaced from said wall of said closed container and being in substantial alignment with said wall and spatial configuration of said closed container;

means for inserting and removing an object from the spatial volume provided by said superabsorbent fibrous lining within said closed container;

spacing means disposed within said closed container for maintaining at least a portion of said superabsorbent fibrous lining at a spaced distance from said wall of said closed container;

first on-demand means disposed at least partially within said spaced distance for introducing a freezible liquid to said superabsorbent fibrous lining on-demand, such freezible liquid as is introduced via said first on-demand means being absorbed by said superabsorbent fibrous lining; and second on-demand means-disposed at least partially within said spaced distance for introducing a refrigerant gas to said superabsorbent fibrous lining on-demand, such refrigerant gas as is introduced via said second on-demand means causing the freezing—of such liquids as have been absorbed by said superabsorbent fibrous lining.

4. A portable, superabsorbent carrying container able to provide refrigeration on-demand for its contents, said carrying container comprising:

a portable, closed container comprising at least one wall and having a determinable internal volume and spatial configuration;

at least one superabsorbent fibrous lining disposed within the internal volume of said closed container;

a freezible solid coating applied to at least a portion of said superabsorbent fibrous lining within said closed container;

means for inserting and removing an object from the spatial volume provided by said coated superabsorbent fibrous lining within said closed container; and on-demand means in communication with the internal volume of said closed container for introducing a refrigerant gas to said coated superabsorbent fibrous lining on-demand, such refrigerant gas as is introduced via said on-demand means causing the freezing of said solid coating of said superabsorbent fibrous lining.

5. A portable, superabsorbent carrying container able to provide refrigeration on-demand for its contents, said carrying container comprising:

a portable, closed container comprising at least one wall and having a determinable internal volume and spatial configuration;

at least one superabsorbent fibrous lining disposed within the internal volume of said closed container, said superabsorbent fibrous lining being at least in part internally spaced from said wall of said closed container and being in substantial alignment with said wall and spatial configuration of said closed container;

a freezible solid coating applied to at least a portion of said superabsorbent fibrous lining within said closed container;

means for inserting and removing an object from the spatial volume provided by said coated superabsorbent fibrous lining within said closed container;

spacing means disposed within said closed container for maintaining at least a portion of said coated superabsorbent fibrous lining at a spaced distance from said wall of said closed container; and on-demand means in communication with said spaced distance for introducing a refrigerant gas to said coated superabsorbent fibrous lining on-demand, such refrigerant gas as is introduced via said on-demand means causing the freezing of said solid coating of said superabsorbent fibrous lining.

6. The superabsorbent carrying container as recited in claim 1, 2, 3, 4, or 5 wherein said superabsorbent fibrous lining is in substantial alignment with said wall and said spatial configuration of said closed container.

7. The superabsorbent carrying container as recited in claim 3 further comprising:

a portable source of a freezible liquid in flow communication with said first on-demand means; and a portable source of a refrigerant gas in flow communication with said second on-demand means.

8. The superabsorbent carrying container as recited in claim 4 or 5 further comprising a portable source of a refrigerant gas in flow communication with said on-demand means.

9. The superabsorbent carrying container as recited in claim 1, 2, or 3 wherein said freezible liquid comprises water.

10. The superabsorbent carrying container as recited in claim 4 or 5 wherein said freezible solid coating is a hydrogel.

11. The superabsorbent carrying container as recited in claim 1, 2, 3, 4, or 5 wherein said refrigerant gas is compressed carbon dioxide.

12. The superabsorbent carrying container as recited in claim 1, 2, 3, 4, or 5 wherein said refrigerant gas is selected from the group consisting of compressed nitrogen, oxygen, and fluorocarbon gases.

13. The superabsorbent carrying container as recited in claim 1, 2, 3, 4, or 5 wherein said closed container is fluidimpermeable.

* * * * *